US009782744B2

(12) United States Patent
Warner et al.

(10) Patent No.: US 9,782,744 B2
(45) Date of Patent: Oct. 10, 2017

(54) DETECTION AND MOLECULAR WEIGHT DETERMINATION OF ORGANIC VAPORS

(75) Inventors: Isiah M. Warner, Baton Rouge, LA (US); Bishnu P. Regmi, Baton Rouge, LA (US); Bilal El-Zahab, Miami Beach, FL (US); Daniel J. Hayes, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 1120 days.

(21) Appl. No.: 13/980,068

(22) PCT Filed: Jan. 19, 2012

(86) PCT No.: PCT/US2012/021806
§ 371 (c)(1),
(2), (4) Date: Jul. 17, 2013

(87) PCT Pub. No.: WO2012/158214
PCT Pub. Date: Nov. 22, 2012

(65) Prior Publication Data
US 2013/0303402 A1    Nov. 14, 2013

Related U.S. Application Data

(60) Provisional application No. 61/434,660, filed on Jan. 20, 2011, provisional application No. 61/434,879, filed on Jan. 21, 2011.

(51) Int. Cl.
*B01J 20/22* (2006.01)
*G01N 33/00* (2006.01)
*G01N 29/02* (2006.01)
*G01N 29/036* (2006.01)

(52) U.S. Cl.
CPC ............ *B01J 20/22* (2013.01); *G01N 29/022* (2013.01); *G01N 29/036* (2013.01); *G01N 33/0047* (2013.01); *G01N 2291/021* (2013.01); *G01N 2291/0426* (2013.01)

(58) Field of Classification Search
CPC ....................................................... B01J 20/22
See application file for complete search history.

(56) References Cited

U.S. PATENT DOCUMENTS 4,748,366 A    5/1988 Taylor ............................ 310/328
2010/0251802 A1    10/2010 Patel et al. ................... 73/19.1

FOREIGN PATENT DOCUMENTS

WO    WO 2009/082618    7/2009

OTHER PUBLICATIONS

Hwang et al., "Recognition of alcohol vapor molecules by simultaneous measurements of resistance changes on polypyrrole-based composite thin films and mass changes on a piezopelectric crystal" Sensors and Actuators B, vol. 75, pp. 67-75 (2001).*
Holloway, A.F. et al., "New Method of Vapour Discrimination Using the Thickness Shear Mode (TSM) Resonator," Sensors, vol. 3, pp. 187-191 (2003).
Hwang, B.J., "Recognition of Alcohol Vapor Molecules by Simultaneous Measurements of Resistance Changes on Polypyrrole-based Composite Thin Films and Mass Changes on a Piezoelectric Crystal," Sensos and Actuators B, vol. 75, pp. 67-75 (2001).
Lin, C.W. et al., "Characteristics and Sensing Behavior of Electrochemically Codeposited Polypyrrole-Poly(Vinyl alcohol) Think Film Exposed to Ethanol Vapors," J. of App. Polymer Sc., vol. 73, pp. 2079-2087 (1999).
Martin, S.J. et al., "Utilization of Polymer Viscoelastic Properties in Acoustic Wave Sensor Applications," Solid-State Sensor and Actuator Workshop, 4th Technical Digest., IEEE, pp. 98-101 (Jun. 4-7, 1990).
Nomani, Md. W.K. et al., "Highly sensitive and multidimensional detection of $NO_2$ using $In_2O_3$ thin films," Elsevier, vol. 160, Iss. 1, pp. 251-259 (2011).
Qazi, Muhammad et al., "Two-dimensional signatures for molecular identification," Applied Physics Letters, vol. 92, pp. 103120-1-103120-3 (2008).
Snow, E.S. et al., "Capacitance and Conductance of Single-Walled Carbon Nanotubes in the Presence of Chemical Vapors," Nano Letters, vol. 5, No. 12, pp. 2414-2417 (2005).
Tesfai, A. et al., "Magnetic and Nonmagnetic Nanoparticles from a Group of Uniform Materials Based on Organic Salts," ACS Nano, vol. 3, No. 10, pp. 3244-3250 (2009).

* cited by examiner

*Primary Examiner* — Robert Harlan
(74) *Attorney, Agent, or Firm* — John H. Runnels

(57) ABSTRACT

Composite films comprising an organic salt (or GUMBOS) such as 1-n-butyl-2,3-dimethylimidazolium hexafluorophosphate and a polymer such as cellulose acetate are prepared. These films are useful in detecting vapors of volatile organic compounds, and in determining their molecular weights. A quartz crystal microbalance-based sensor was designed by depositing a thin film of this composite material on the gold electrode surface of a quartz crystal resonator. The sensor exhibited rapid response toward a variety of volatile organic compounds, and complete regeneration, high sensitivity, low detection limits, and wide dynamic ranges. The ratio of the change in frequency to the change in motional resistance is a concentration-independent quantity that is proportional to the molecular weight of the absorbed chemical species. These properties facilitate the easy identification and molecular weight determination of a broad range of organic vapors.

9 Claims, 15 Drawing Sheets

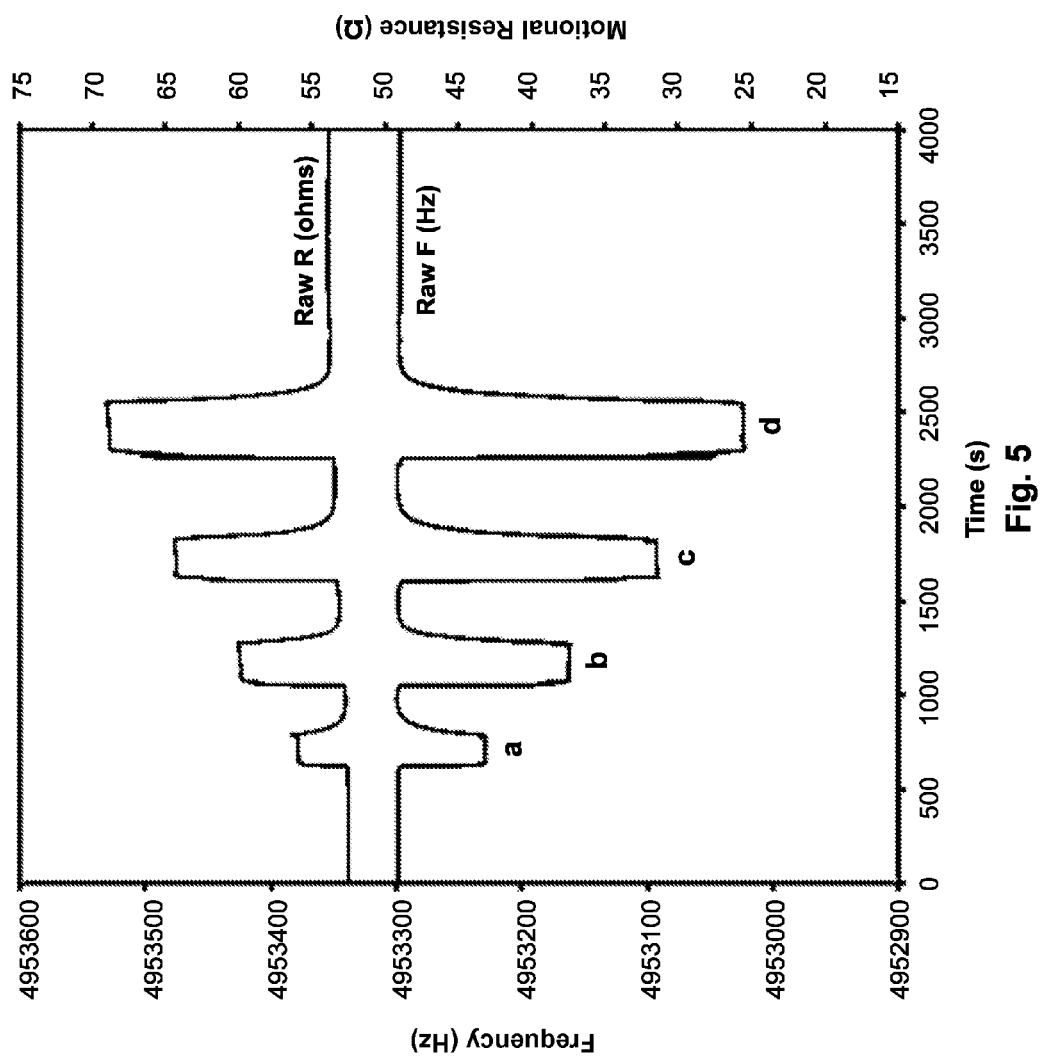

DETECTION AND MOLECULAR WEIGHT DETERMINATION OF ORGANIC VAPORS

This is the United States national stage of international application PCT/US2012/021806, international filing date Jan. 19, 2012, which claims the benefit of the Jan. 20, 2011 filing date of U.S. provisional patent application Ser. No. 61/434,660; and of the Jan. 21, 2011 filing date of U.S. provisional application Ser. No. 61/434,879 under 35 U.S.C. §119(e). The complete disclosures of both priority applications are hereby incorporated by reference in their entirety.

This invention was made with government support under grant CHE-0911118 awarded by the National Science Foundation, and grant 1R01GM079670 awarded by the National Institutes of Health. The United States Government has certain rights in this invention.

TECHNICAL FIELD

This invention pertains to GUMBOS-based composite materials, and their use for detection and molecular weight determination of gases.

BACKGROUND ART

The development of cost-efficient, portable, and sensitive detection systems for volatile organic compounds (VOCs) has become increasingly important. VOC sensors have extensive utility in environmental monitoring, health care, agriculture, food safety, defense, and homeland security applications. Many sensing technologies have been used for detection of VOCs, including differential ion mobility spectrometry, gas chromatography-mass spectrometry, photoionization, laser desorption mass spectrometry, nanowire coatings, and cantilever detectors. Devices based on the sorption of gas molecules are increasingly being adopted because of their simplicity, compactness, and amenability to use with sensor arrays. Sorption-based sensors have a chemosensitive coating that selectively and reversibly sorbs analytes of interest. To achieve optimal measurement of the analyte, sensing materials are often immobilized directly onto the surface of a transducer that converts the binding event into an electronic signal. Mechanical oscillators, chemicapacitors, and chemiresistors are often the transducers of choice for analyses of a broad range of chemical vapors.

A quartz crystal microbalance (QCM) is a common piezoelectric transducer that can be used as a sorption-based sensor. The operating principle of this sensor is based on the alteration of the characteristics of acoustic shear waves propagating through the piezoelectric material. A QCM typically comprises a thin slice of AT-cut quartz wafer that is sandwiched between two electrodes. When an oscillating electric voltage is applied perpendicular to the surface of the quartz resonator, an acoustic shear wave is produced that propagates across the thickness of the crystal. As the sorbent coating interacts with the analyte, its mass and mechanical properties are altered, which in turn leads to a phase shift and attenuation of the shear wave propagating through the film adhering to the electrode surface. This phase shift leads to a change in resonance frequency, which depends on the mass of added material on the surface of the resonator. The frequency shift, $\Delta f$, and the added mass, $\Delta m$, of the analyte are related according to the Sauerbrey equation:

$$\Delta f = -\frac{2\Delta m f^2}{A(\mu \rho_q)^{\frac{1}{2}}} = -C_f \Delta m \quad \text{(Equation 1)}$$

where f is the intrinsic frequency of the quartz crystal, A is the active vibrating area, $\mu$ is the shear modulus of quartz ($2.95 \times 10^{11}$ dyne/cm$^2$), $\rho_g$ is the density of quartz (2.65 g/cm$^3$), and $C_f$ is the integrated QCM sensitivity (i.e., collecting all the factors except $\Delta m$). The Sauerbrey equation is valid in the regime where the adsorbed mass is small as compared to the overall mass of the crystal, and the additional mass is rigidly bound and evenly distributed over the electrode's surface. Attenuation of the shear wave is due to dissipation of energy during oscillation. This attenuation can be estimated by measuring an electrical property called motional resistance, R, of the QCM. Thin and rigid films display less dissipation and hence produce a small increase in R, while thick and viscoelastic films exhibit high dissipation and a correspondingly large increase in R.

Various sensing materials, including polymers, inorganic oxides, polymer/carbon black composites, carbon nanotubes, graphite microparticles, amino acids, $TiO_2$-porphyrin nanocomposites, calixarenes, lipids, and room temperature ionic liquids (RTILs), have been used in formulating chemosensitive QCM coatings to detect and identify a range of VOCs.

Ionic liquids (ILs) are usually defined as organic salts that melt below 100° C. ILs that are liquid at or below room temperature are commonly known as RTILs, whereas those in the solid state, i.e. room temperature to 100° C., are often referred to as 'frozen' ILs.

The use of RTILs as sensing materials is relatively recent. The unique combination of thermal and chemical stability with tunable physico-chemical properties has led to the use of RTILs for gas sensing applications. Short response time and high reversibility are properties of QCM/RTIL sensors. However, the use of RTILs as gas sensors has two major limitations: de-wetting of a film coating to form macroscopic drops; and the well-known viscosity-density effect. The absorption of organic vapor into RTILs causes a decrease in the density and viscosity of the liquid, leading to an increase in frequency—the so-called viscosity-density effect. To overcome these drawbacks, very thin RTIL coatings have sometimes been used. The thin coatings behave as quasi-rigid layers, and hence exhibit a decrease in frequency upon analyte sorption. The use of thin films, however, limits the sensitivity of the sensor, because the amount of vapor that can be absorbed depends on the quantity of the sorbent material deposited on the surface.

"GUMBOS" are compounds from a Group of Uniform Materials Based on Organic Salts. The acronym GUMBOS includes both frozen ILs (those with melting points from 25° C. to 100° C.) and analogous organic salts that melt from 100° C. to 250° C. See A. Tesfai, B. El-Zahab, A. T. Kelley, M. Li, J. C. Garno, G. A. Baker, I. M. Warner, ACS Nano 2009, 3, 3244; and published international patent application WO 2009/082618. "GUMBOS" is defined to mean an organic salt having a melting point between 25° C. and 250° C. (The word "GUMBOS" may be either singular or plural.)

A. F. Holloway, A. Nabok, M. Thompson, A. K. Ray, D. Crowther, J. Siddiqi, Sensors 2003, 3, 187 reported using calyx[4]resorcinarene films with QCM to measure $\Delta f$ and $\Delta R$, distinguishing between hexane and toluene vapors. While the authors reported measurements of $\Delta f$ and $\Delta R$, they did not report any correlation between $\Delta f/\Delta R$ and the physico-chemical properties of the analytes.

DISCLOSURE OF THE INVENTION

We have discovered novel composite materials and methods for the detection, discrimination, and molecular weight determination of organic vapors via piezoelectric measurements. The novel apparatus and method employ a composite film containing one or more GUMBOS, deposited on a piezoelectric crystal microbalance. The novel apparatus and method have excellent properties for detecting and characterizing organic vapors.

Besides the GUMBOS component, the other component of the composite (typically a polymer) acts to inhibit crystallization of the GUMBOS and to modulate the viscoelastic properties of the GUMBOS, so that the composite has a linear relationship between $\Delta f/\Delta R$ and the molecular weight of absorbed compounds. The composite material is viscoelastic; and the viscoelastic characteristics of the composite material are substantially different from what the viscoelastic characteristics of the GUMBOS alone would be, if the GUMBOS were not intermixed with one or more polymers. The GUMBOS is amorphous within said composite material. In our prototype embodiment, the other component of the composite was a polymer, cellulose acetate. We believe that the cellulose acetate provided a fibrous scaffold upon which the GUMBOS could deposit, and in doing so improve the viscoelastic behavior of the film. In addition to cellulose acetate, we have also seen similar behavior with cellulose acetate butyrate. Other polymers known in the art may also be used in forming GUMBOS-containing composites. Preferred polymers for this purpose are polyelectrolytes, or polymers otherwise containing polar groups; but even nonpolar polymers may be used in forming the composites. Preferred polyelectrolytes, include for example the following polycations and polyanions:

Polycations:
Poly(allylamine)
Poly(2-ethyl-2-oxazoline)
Poly(acrylamide-co-diallyldimethylammonium chloride)
Poly[bis(2-chloroethyl)ether-alt-1,3-bis[3-(dimethylamino) propyl]urea]quaternized
Poly(dimethylamine-co-epichlorohydrin-co-ethylenediamine)
Poly(2-dimethylamino)ethyl methacrylate) methyl chloride
Poly(p-xylene tetrahydrothiophenium chloride)
Poly(diallyldimethylammonium chloride)
Poly-L-Lysine
Poly(ethyleneimine)
Poly(amido amine) dendrimer
Poly-L-ornithine
Polybrene
Poly-arginine
Chitosan
Polyanions:
Poly(vinyl sulfate)
Poly(sodium 4-styrenesulfonate)
Polyanetholesulfonic acid
Poly(4-styrenesulfonic acid-co-maleic acid)
Poly(2-acrylamido-2-methyl-1-propanesulfonic acid)
Poly(2-acrylamido-2-methyl-1-propanesulfonic acid-co-acrylonitrile)
Polyinosinic-polycytidylic acid
Poly(methacrylic acid)
Poly(styrenesulfonic acid)
Poly(vinylsulfonic acid, sodium salt)
Poly[1-[4-(3-carboxy-4-hydroxyphenylazo)benzenesulfonamido]-1,2-ethanediyl, sodium salt]
Poly(2'-deoxyadenylic acid)
Poly(deoxyadenylic-thymidylic) acid
Poly-D-glutamic acid
Poly(ethylene-co-methacrylic acid)
Polycytidylic acid
Poly-L-aspartic acid
Poly(guanylic-uridylic) acid In a prototype embodiment, we have prepared, investigated, and characterized the vapor sensing characteristics of a thin composite film comprising cellulose acetate (CA), which has a glass transition temperature of 67° C., and a representative GUMBOS: 1-n-butyl-2,3-dimethylimidazolium hexafluorophosphate ([BM$_2$Im][PF$_6$]), which has a melting point of 43° C. and a glass transition temperature of −58° C. A film of the composite material on a gold substrate was prepared by co-deposition of [BM$_2$Im][PF$_6$] and CA. The film has been characterized by scanning electron microscopy (SEM), laser scanning confocal microscopy (LSCM), powder X-ray diffraction (XRD), Fourier transform infrared (FTIR) spectroscopy, and electron probe microanalysis with wavelength dispersive spectroscopy (EPMA-WDS). Classical molecular dynamics (MD) simulations for systems containing [BM$_2$Im][PF$_6$], CA, and one of several VOCs were also performed to theoretically model the interactions between these species.

The novel thin composite films have been deposited as a composite onto the gold electrode of a QCM device, which has then successfully been used for detecting and discriminating VOCs. The response of the resultant QCM sensor toward a variety of organic vapors was measured. The novel composite-coated sensor exhibited rapid response, high sensitivity, low detection limits, wide dynamic ranges, and complete regeneration. Changes in the viscoelastic properties of the film upon sorption of various analyte vapors were determined by simultaneously monitoring both $\Delta f$ and motional resistance shift ($\Delta R$). Analysis of these data at low to moderate vapor absorptions revealed the surprising discoveries that the ratio $\Delta f/\Delta R$ is nearly constant for a particular vapor, and that this ratio depends directly upon the molecular weight of the absorbed chemical species. This surprising finding allows QCM with GUMBOS composite films to be used in identifying and quantifying a wide variety of analytes.

While quartz is preferred, other crystals of other piezoelectric materials known in the art may also be used in practicing this invention, including for example gallium orthophosphate or langasite.

BRIEF DESCRIPTION OF THE DRAWINGS

FIG. 1(a) depicts a film of approximately 73 μg/cm$^2$ [BM$_2$Im][PF$_6$] alone. FIG. 1(b) depicts a film of approximately 83 μg/cm$^2$ of the [BM$_2$Im][PF$_6$]/CA composite. FIG. 1(c) depicts a film of approximately 214 μg/cm$^2$ of the [BM$_2$Im][PF$_6$]/CA composite.

FIG. 5 depicts the frequency and resistance responses of a prototype QCM sensor to four different concentrations of chloroform vapor over a course of time: (a) 17.8 mg/L, (b) 35.6 mg/L, (c) 53.4 mg/L, and (d) 71.3 mg/L. The amount of coating material was 207 μg/cm$^2$. The upper curve depicts motional resistance response, and the lower curve depicts frequency response.

MODES FOR CARRYING OUT THE INVENTION

Materials and Methods

Example 1. Materials

Figure 1A:
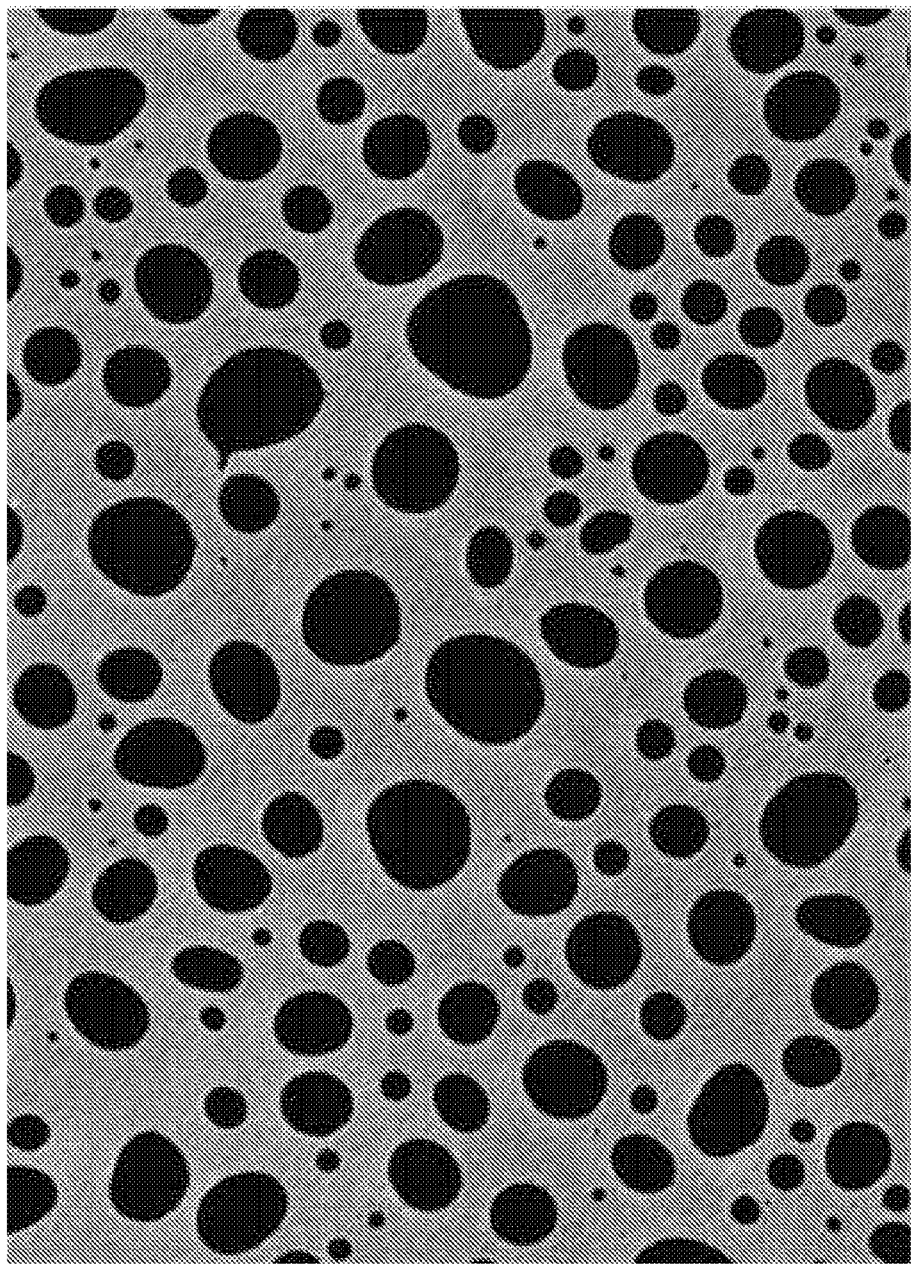
FIGS. 1(a)-(c) depict SEM micrographs of GUMBOS films deposited on gold surfaces.

[BM$_2$Im][PF$_6$], [BM$_2$Im][OTf], and [BMPyr][PF$_6$] were obtained from Ionic Liquids Technologies, Inc. as crystalline solids. [EM$_2$Im][PF$_6$] (crystalline solid), cellulose acetate (molecular weight 30,000 Da), cellulose acetate butyrate (molecular weight 30,000 Da), anhydrous heptane, anhydrous acetonitrile, anhydrous chloroform, anhydrous carbon tetrachloride, and anhydrous toluene were obtained from Sigma-Aldrich. Acetone, n-propanol, and anhydrous methanol were obtained from Mallinckrodt Chemicals, and absolute ethanol was obtained from Pharmco. All reagents were used as received.

The QCM200 controller and associated quartz crystals were purchased from Stanford Research Systems, Inc., Sunnyvale, Calif. The crystals were 5-MHz AT-cut chromium/gold polished crystals, 1.00 inch (2.54 cm) diameter. Gold-coated silicon wafers were obtained from Sigma Aldrich. Polytetrafluoroethylene (PTFE) containers used in these experiments were obtained from SPI Supplies/Structure Probe, Inc. United States.

Example 2. Preparation of Stock Solutions

Stock solutions of [BM$_2$Im][PF$_6$] (1 mg/mL) and cellulose acetate (0.5 mg/mL) in acetone were prepared in 20-ml borosilicate glass scintillation vials. Particulate matter was removed by successive filtration using a glass syringe with a stainless steel filter holder and a Whatman 0.45 μm PTFE/GMF syringe filter.

Example 3. Cleaning of Gold Surface

The QCM crystal (or gold-coated silicon wafer) was rinsed with distilled water and ultrasonicated in acetone for 5 minutes; and then dried under flowing nitrogen gas. The crystal was then immersed in fresh "piranha" solution (3:1 concentrated sulfuric acid and 30% hydrogen peroxide) for 10 minutes, washed with copious amounts of distilled water, rinsed with acetone, and dried under a stream of nitrogen. The crystal was further dried in an oven at 100° C., and allowed to cool to room temperature. Cleaned crystals were coated immediately.

Example 4. Preparation of Films

Coatings were prepared by a solvent precipitation method. To 2 mL of a solution containing various concentrations of [BM$_2$Im][PF$_6$], 6 mL of anhydrous heptane was added dropwise with stirring. (In the case of the composite, the mass proportion of [BM$_2$Im][PF$_6$] and cellulose acetate in the solution was initially varied. The optimal mass [BM$_2$Im][PF$_6$]-to-CA mass ratio was found to be about 7.5:1, a ratio that was then maintained in further experiments.) The mixture was then transferred to a 25-mL PTFE beaker. A cleaned quartz crystal was immersed in the mixture and allowed to incubate for six hours. The crystal was then ultrasonicated for one minute, while being held vertically in a fresh pool of heptane, to remove any loosely adhered material. The coated crystal was then stored in a desiccator for a minimum of 24 hours before being mounted in the crystal holder. A similar procedure was used for coating the surface of the gold-coated silicon substrate.

Example 5. Characterization of Film Coatings

SEM Analysis:
A film was imaged using a JEOL JSM-6610 scanning electron microscope in high-vacuum mode.

LSCM Analysis:
The heights of the droplets were analyzed using a Leica TCS SP2 laser scanning confocal microscope in reflection mode, using a 488-nm laser.

Powder X-Ray Diffraction Analysis:
Powder XRD data of the films deposited on gold surface or glass surface were collected using a Bruker/Siemens D5000 automated powder X-ray diffractometer, using Cu Kα radiation and a scintillation point detector. The operating conditions were set at 40 kV and 30 mA, and the data were recorded over a 2θ range from 2° to 70° at intervals of 0.02°, taken at 1 second per step.

FTIR Analysis:
IR spectra of the films were recorded on a Bruker Tensor 27 spectrometer equipped with a PIKE MIRacle single-bounce attenuated total reflectance (ATR) cell. Spectra were collected over the 3600-530 cm$^{-1}$ region with 256 scans at a resolution of 4 cm$^{-1}$. FTIR data were analyzed using OPUS 6.5 software.

Electron Probe Microanalysis:
EPMA of the films was performed with a JEOL Superprobe 733, equipped with a wavelength dispersive spectrometer (WDS), using an accelerating voltage of 15 kV, a probe current of 10 nA, and a beam diameter of 30 microns. Nine different spots in each film and a blank substrate were analyzed.

Example 6. Data Acquisition

Figure 7:
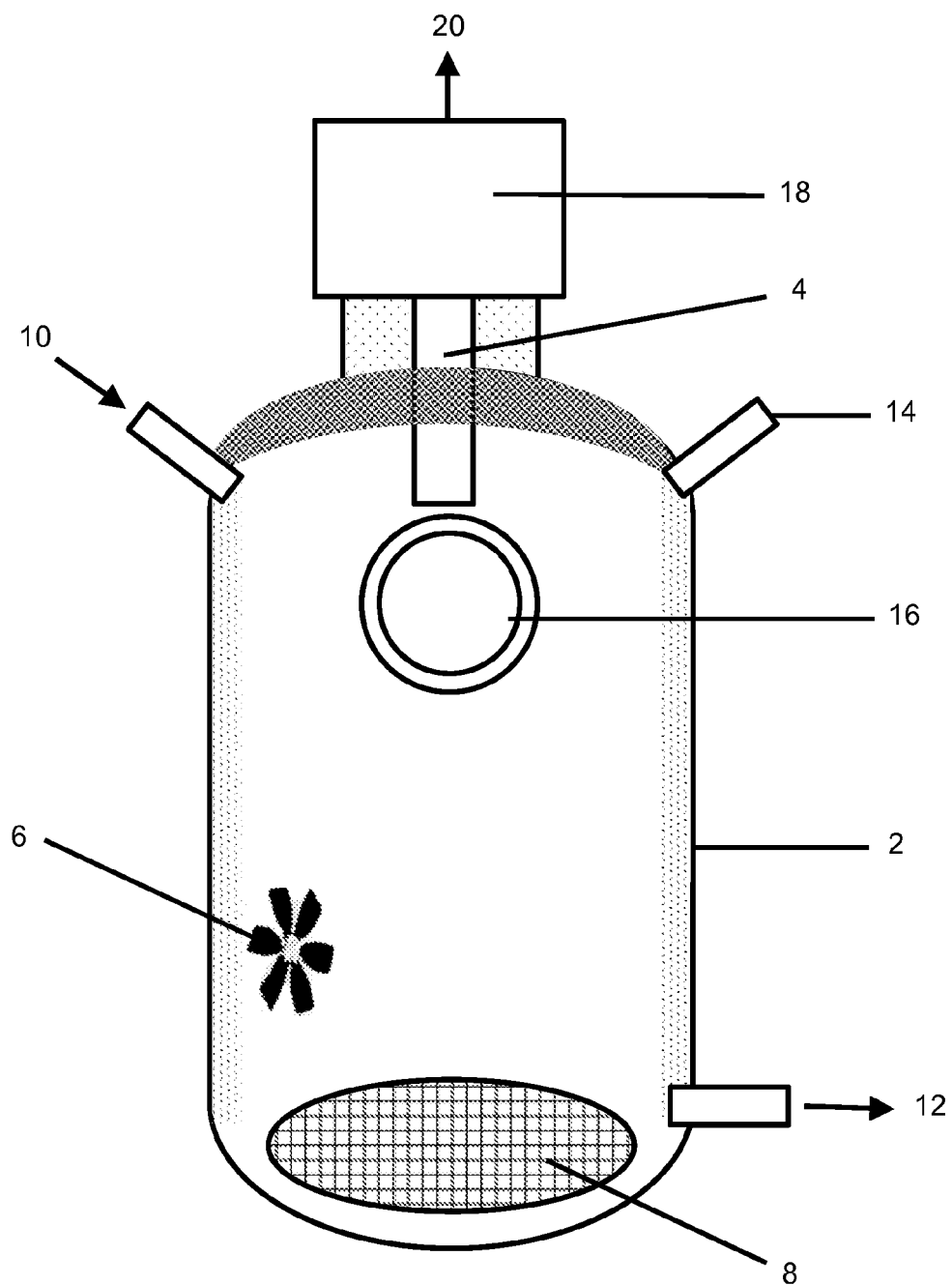
FIG. 7 depicts a schematic diagram of the experimental setup.

The QCM sensor was exposed to various VOC vapors in a custom-made non-flow system. A schematic diagram of the experimental setup is depicted in FIG. 7. The volume of the chamber 2, less the volume of crystal holder 4, was 4.14 L. The volumes of the fan 6 and filter paper 8 were disregarded. Chamber 2 contained an inlet 10 and an outlet 12 for argon gas; and a rubber septum 14 for sample introduction. Ultrapure argon was intermittently blown through the container until stable frequency and motional resistance were obtained. After achieving equilibrium, the argon inlet and outlet were closed; and a known volume of liquid organic sample was injected into the closed container 2 using a Hamilton microsyringe (not shown). The rate of evaporation was enhanced by dropping the sample onto filter paper 8, and the vapor was homogenized using small fan 6. The frequency and resistance shifts of coated crystal 16, which was driven by QCM25 crystal oscillator 18, were measured following the introduction of analyte vapor. The data 20 were output to a QCM200 digital controller and a digital computer (not shown). The static capacitance, $C_o$, of the instrument was nullified to obtain the true values of resonance frequency and motional resistance. The concentration of analyte was successively increased to produce a response curve. The introduction of analyte into the chamber produced an increase in overall pressure, but this small pressure change was found to have a negligible effect on both frequency and motional resistance. All experiments were performed in a temperature-controlled room at 22° C. Temperature fluctuations during experiments were measured to be below ±0.2° C. Sample vapors were removed following a measurement by blowing a gentle stream of ultrapure argon gas through the container until the baseline values were recovered.

Example 7. Molecular Dynamics Simulations

Classical MD simulations were performed with the GROMACS MD package in the NPT ensemble. See B. Hess, C. Kutzner, D. van der Spoel, E. Lindahl, *J. Chem. Theory Comput.* 2008, 4, 435. The isotropic pressure coupling with a time constant of 0.2 ps was controlled by a Berendsen barostat. The improved velocity-rescaling algorithm recently proposed by Parrinello et al. was used to mimic weak thermal coupling with a coupling constant of 0.05 ps. See G. Bussi, D. Donadio, M. Parrinello, *J. Chem. Phys.* 2007, 126, 014101; and G. Bussi, T. Zykova-Timan, M. Parrinello, *J. Chem. Phys.* 2009, 130, 074101. In all simulations, Lennard-Jones interactions were cutoff at 1.2 nm, and long-range Coulomb interactions were handled by the particle-mesh Ewald (PME) method with a cutoff of 1.0 nm and a grid spacing of 0.1 nm. See D. Y. Tom Darden, and Lee Pedersen, *J. Chem. Phys.* 1993, 98, 10089. Periodic boundaries were applied in all directions. In all simulations, H-bond lengths were constrained with the LILACS algorithm. See B. Hess, H. Bekker, H. J. C. Berendsen, J. Fraaije, *J. Comput. Chem.* 1997, 18, 1463.

The system modeled in these simulations contained 500 pairs of [BM$_2$Im][PF$_6$], and 18 oligomers of CA, with a mass ratio between the two of 7.5:1 (the same as that of the experiments). A single molecule of analyte was added to the simulation box. Six different analytes used in the experiments were considered in different simulations: acetone, acetonitrile, chloroform, ethanol, methanol, and toluene. All parameters used for modeling were selected from force fields available in the literature. Intramolecular parameters (bond lengths, valence angles, and torsional profiles) and intermolecular parameters (Lennard-Jones terms and electrostatic charges) were chosen from the OPLS-AA force field for [BM$_2$Im]$^+$, [PF$_6$]$^-$, CA, and the six analytes. See W. L. Jorgensen, D. S. Maxwell, J. Tiradorives, *J. Am. Chem. Soc.* 1996, 118, 11225 Coulomb interactions were represented by partial charges placed on the atomic sites as defined by Lopes and Padua and Jorgensen. See J. N. C. Lopes, J. Deschamps, A. A. H. Padua, *J. Phys. Chem. B* 2004, 108, 2038; J. N. C. Lopes, A. A. H. Padua, K. Shimizu, *J. Phys. Chem. B* 2008, 112, 5039; and W. L. Jorgensen, D. S. Maxwell, J. Tiradorives, *J. Am. Chem. Soc.* 1996, 118, 11225.

Simulations were performed at 350° K, a temperature at which [BM$_2$Im][PF$_6$] is in the liquid phase. By running the simulation at such a high temperature, all molecules in the system had greater thermal mobility, thus allowing the sampling of properties of interest using shorter simulations. The simulations were run at 350° K for 2 ns for equilibration, and the properties of interest were then observed during another 2 ns. We also ran two, 4 ns simulations at 295° K (the actual experimental temperature), and found minimal changes in the trends of the properties of interest. To determine the electrostatic and van der Waals energies in GROMACS, the following energy groups were defined: the molecule of VOC, the ions [BM$_2$Im]$^+$, [PF$_6$]$^-$, the CA groups; a single ion of [BM$_2$Im*]$^+$, a single [PF$_6$*]$^-$ ion, and a single CA oligomer, all randomly chosen. The total interaction energy of any given molecule of VOC with the other species in the system (all the [BM$_2$Im]$^+$ and [PF$_6$]$^-$ ions; and all oligomers of CA) was computed in the simulations. The total interaction energy was compared against the total interaction energies experienced by one [BM$_2$Im]$^+$ cation, one [PF$_6$]$^-$ anion and one CA oligomer in the system.

Results and Discussion

The films were prepared using a solvent precipitation method. The chemical constituents that would form the film were dissolved in a binary liquid mixture containing a volatile solvent (acetone) and a less volatile non-solvent (heptane). The non-solvent did not itself dissolve the film-forming constituents. However, it was miscible with the solvent. Preferential evaporation of the solvent left a thin film deposited on the substrate. Both [BM$_2$Im][PF$_6$] and [BM$_2$Im][PF$_6$]/CA composite films were studied, with the former being used primarily for comparison purposes. In the case of the composite, the mass proportion of [BM$_2$Im][PF$_6$] and CA was kept at 7.5:1, which we had determined to be a preferred ratio.

Example 8. Characterization by Scanning Electron Microscopy

Figure 1B:
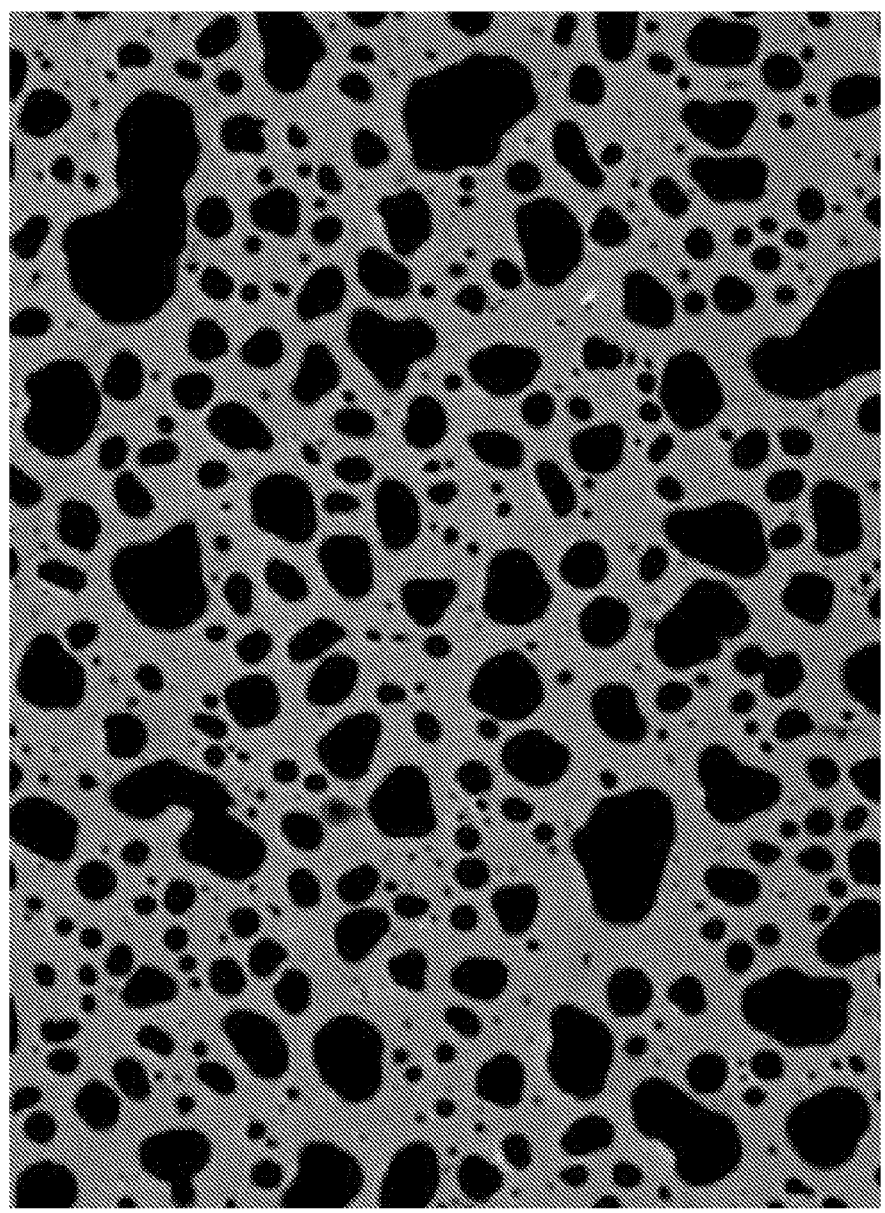
Figure 1C:
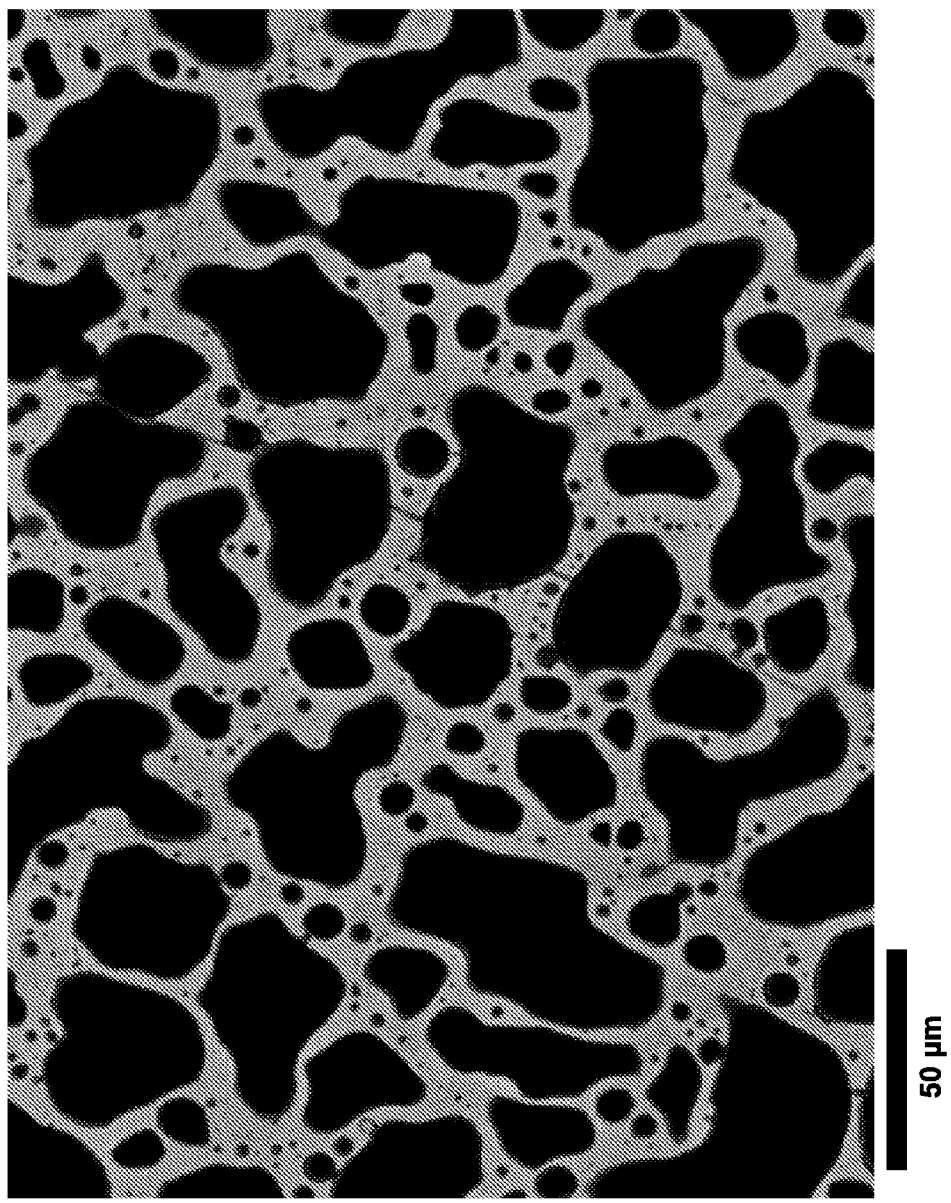

FIGS. 1(a)-(c) display SEM micrographs of films deposited on gold surfaces. FIG. 1(a) depicts a film of approximately 73 μg/cm$^2$ [BM$_2$Im][PF$_6$] alone. FIG. 1(b) depicts a film of approximately 83 μg/cm$^2$ of the [BM$_2$Im][PF$_6$]/CA composite. FIG. 1(c) depicts a film of approximately 214 μg/cm$^2$ of the [BM$_2$Im][PF$_6$]/CA composite.

It is evident from FIGS. 1(a)-(c) that the films were discontinuous, and that they contained isolated microdroplets with a variable size distribution. The shapes of the droplets for pure [BM$_2$Im][PF$_6$] were more regular than those in the composite films. While the droplets may appear to be liquid in the images, we observed that the coating was physically stable and solid. The decrease in frequency and increase in motional resistance observed upon exposure of the films to organic vapors during QCM measurements (discussed below) strongly support the conclusion that the films were in the solid state. By contrast, had the films been liquid, under such high loading conditions the absorption of organic vapor would have produced a positive frequency shift due to a decrease in the viscosity and density of the liquid. Furthermore, a drop in the viscosity and density of a liquid would be expected to decrease the motional resistance, contrary to our actual observations. The height of the droplets, as measured by LSCM, was found to increase with the size (or radius) of the droplets. The maximum height of [BM$_2$Im][PF$_6$] droplets under intermediate loading conditions (FIG. 1a) was approximately 2.6 µm. The maximum height of the [BM$_2$Im][PF$_6$]/CA droplets under similar loading conditions (FIG. 1b) was approximately 2.8 µm. FIG. 1c is an image of the composite film under high loading conditions, showing that the droplets grew in size as the amount of coating material increased. In FIG. 1c the maximum height was approximately 3.2 µm.

Example 9. Characterization by Powder X-Ray Diffraction

Powder XRD measurements of the films deposited on gold-silicon did not reveal any additional peak(s) beyond those of the substrate (data not shown). This observation suggested that both the [BM$_2$Im][PF$_6$] film and the [BM$_2$Im][PF$_6$]/CA film were amorphous. To confirm that there were no coincidental overlaps between diffraction peaks of the films and those of the underlying gold-silicon substrate, films were also prepared on an amorphous glass substrate. The XRD patterns of the films on the glass substrate did not display any sharp peaks, confirming that the films were amorphous (data not shown).

Example 10. Characterization by Infrared Spectroscopy

Figure 2A:
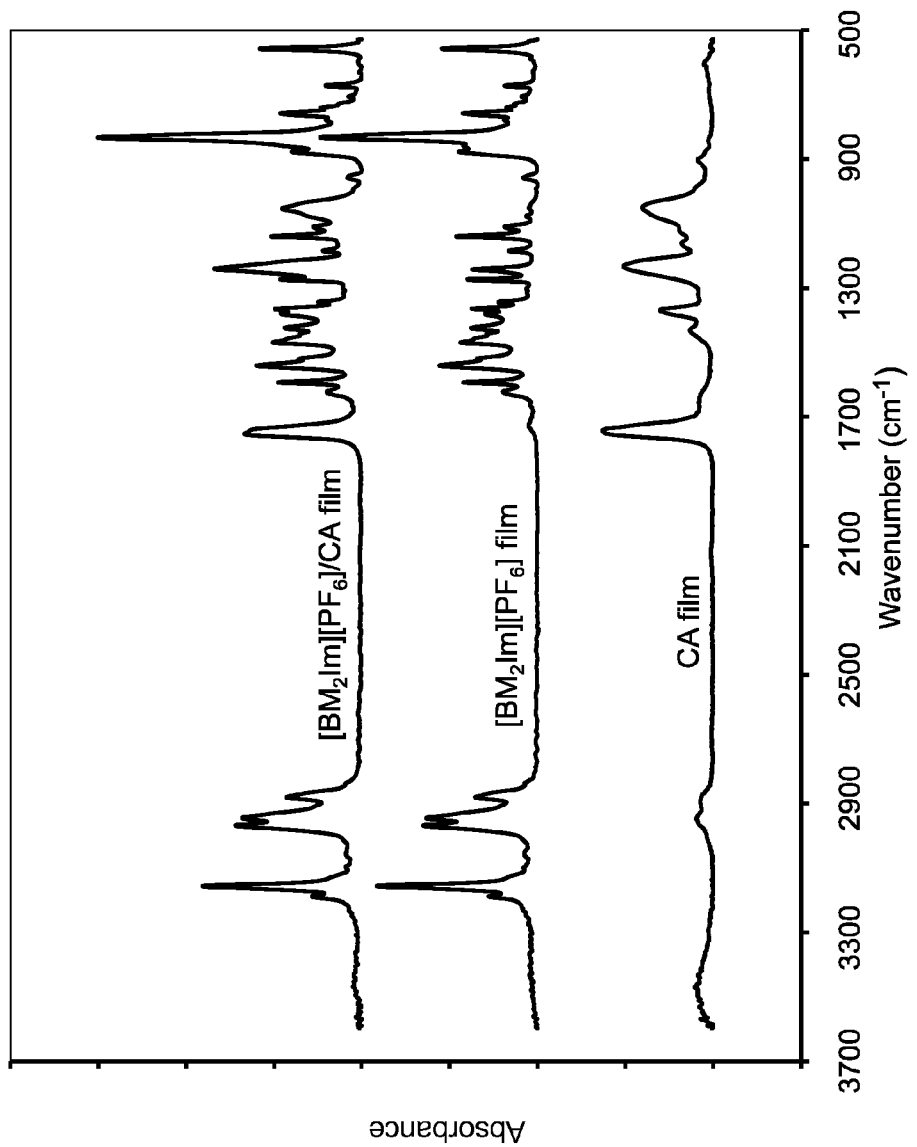
FIG. 2(a) depicts attenuated total reflectance Fourier transform infrared (ATR-FTIR) spectra of CA, [BM$_2$Im][PF$_6$], and [BM$_2$Im][PF$_6$]/CA films.
Figure 2B:
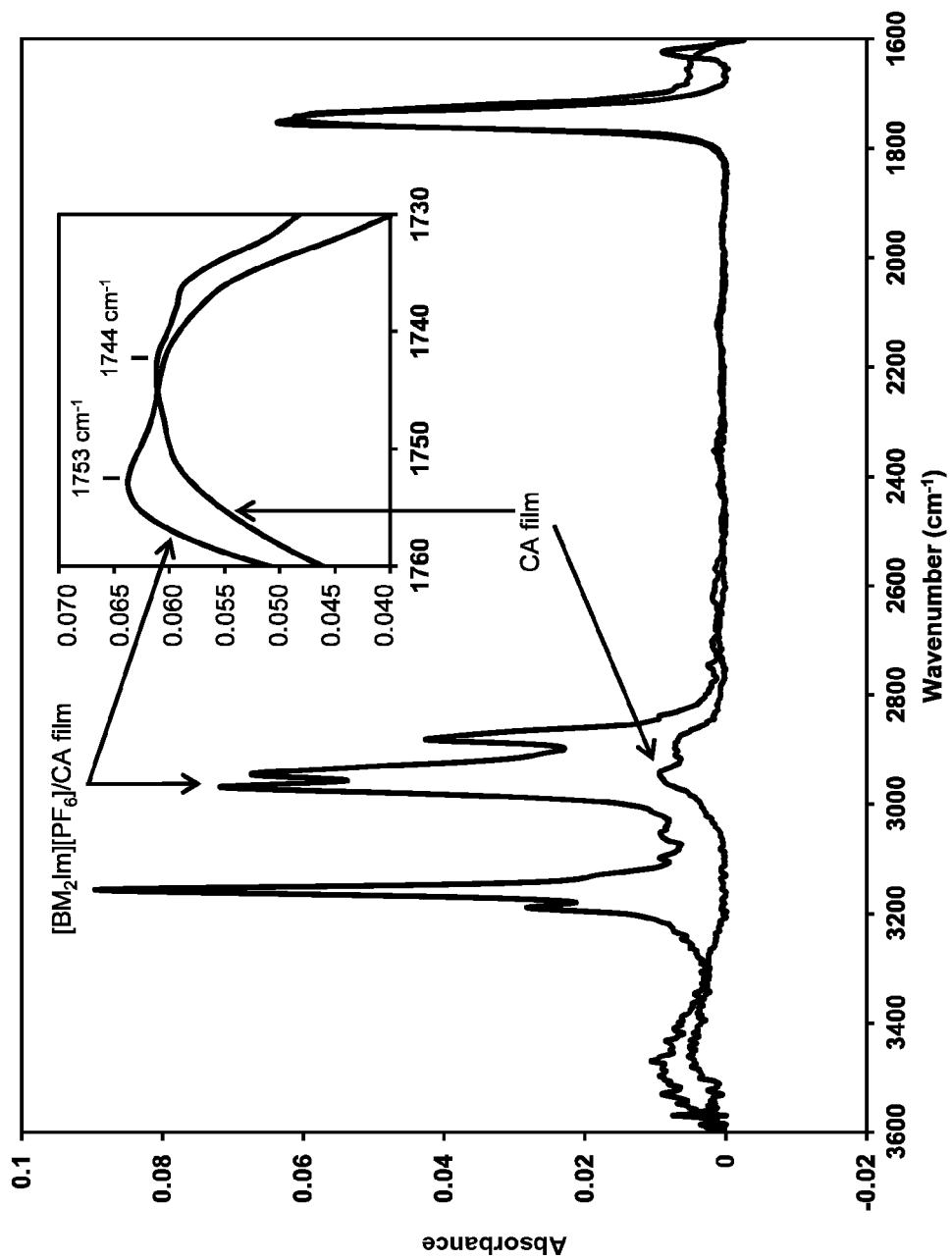
FIG. 2(b) depicts the changes in the IR spectra of the hydroxyl and carbonyl bands. The inset in FIG. 2(b) depicts a magnified plot of the 1760-1730 cm$^{-1}$ region.

Attenuated total reflectance Fourier transform infrared (ATR-FTIR) spectra of CA, [BM$_2$Im][PF$_6$], and [BM$_2$Im][PF$_6$]/CA films are shown in FIG. 2(a). CA can be identified though strong absorption bands with peaks at 1743-1744 cm$^{-1}$ (C=O stretch), 1370 cm$^{-1}$ (C—H bending), 1233 cm$^{-1}$ (C—O stretch, acetyl), and 1051 cm$^{-1}$ (C—O stretch, pyranose ring). [BM$_2$Im][PF$_6$] can be identified though its absorption bands at 3188 cm$^{-1}$ and 3156 cm$^{-1}$ (C—H stretching vibrations of imidazolium ring); 2968 cm$^{-1}$, 2945 cm$^{-1}$ and 2881 cm$^{-1}$ (CH$_3$ stretching); 1592 cm$^{-1}$ (C=C stretching); 1469 cm$^{-1}$ (CH$_3$ bending); 833 cm$^{-1}$ (P—F stretching); and 558 cm$^{-1}$ (F—P—F bending). Absorption bands from [BM$_2$Im][PF$_6$] and from CA were observed in the IR spectrum of the composite film. However, the intensity of the broad band centered around 3500 cm$^{-1}$ (hydroxyl region) decreased, and the C=O stretching band was blue shifted by 9-10 cm$^{-1}$ in the composite film as compared to the corresponding bands for the pure CA film, as shown in FIG. 2b. FIG. 2b depicts the changes in the IR spectra of hydroxyl and carbonyl bands. The inset in FIG. 2b depicts a magnified plot of the 1760-1730 cm$^{-1}$ region. These observations suggested a disruption of some of the hydrogen bonds between CA molecules, and a change in the environment of carbonyl groups. The IR patterns of [BM$_2$Im][PF$_6$], however, showed no strong differences between pure and composite films.

Example 11. Characterization by Electron Probe Microanalysis—Wavelength Dispersion Spectroscopy The [BM$_2$Im][PF$_6$]-to-CA ratio in the composite film was measured by electron probe microanalysis—wavelength dispersion spectroscopy (EPMA-WDS). The phosphorus-to-oxygen (P:O) ratios at nine different 30-µm spots were analyzed. Based on the total P:O ratio, the mass ratio of [BM$_2$Im][PF$_6$] to CA in the film was found to be approximately 7.8:1. Some oxygen background was observed in both the [BM$_2$Im][PF$_6$] film and the blank substrate (gold-coated silicon). Only the "excess" oxygen in the [BM$_2$Im][PF$_6$]/CA film as compared to that in the [BM$_2$Im][PF$_6$] film was attributed to cellulose acetate. Clear variations of P:O ratios were noted in some spots, indicating a heterogeneous distribution of [BM$_2$Im][PF$_6$] and CA on the surface.

Example 12. Evaluation of Vapor Sensing Properties of Films

Figure 3A:
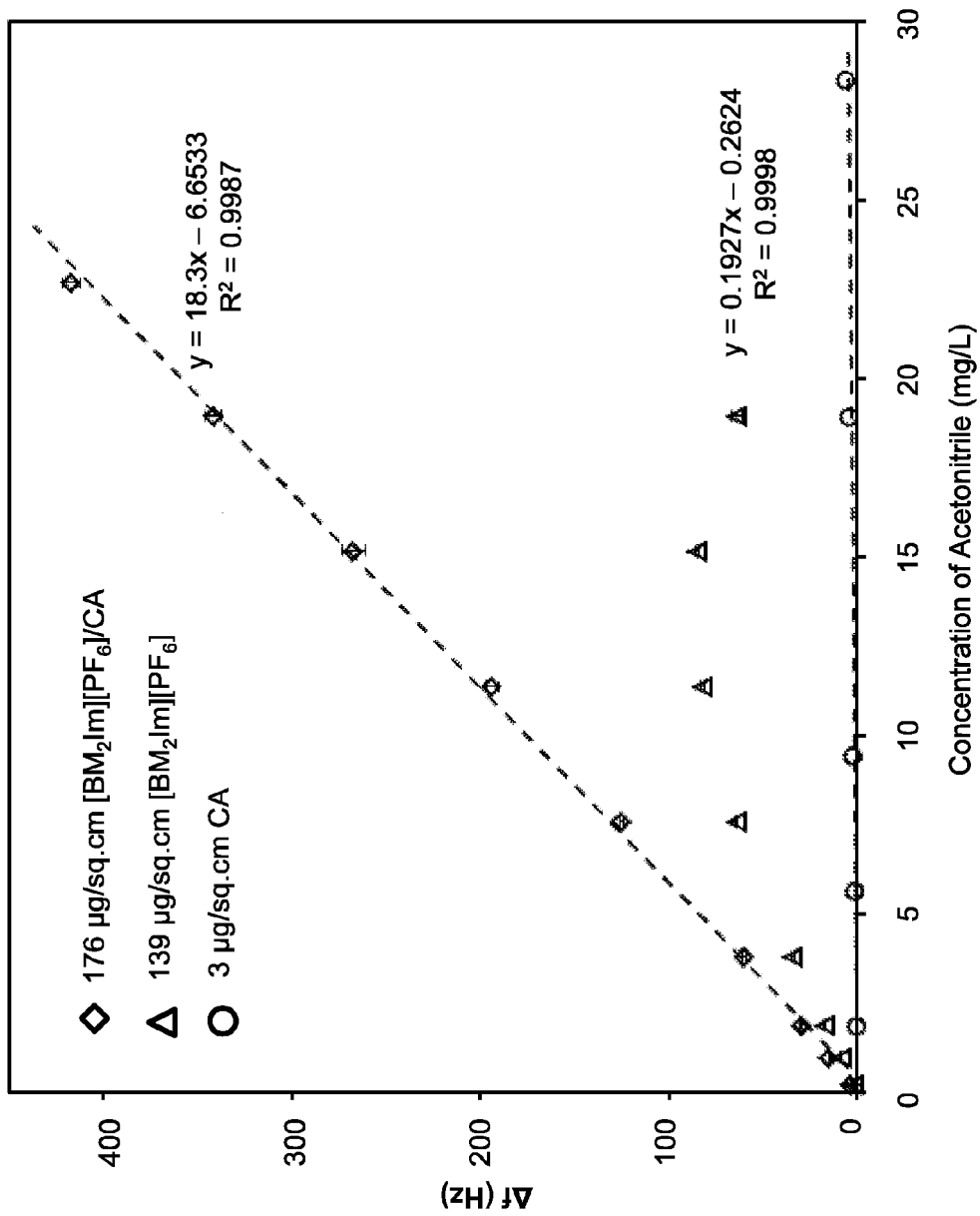
FIG. 3(a) depicts the frequency shift as a function of acetonitrile vapor concentrations for three different coatings: the first prepared using [BM$_2$Im][PF$_6$] only; the second one being a composite with cellulose acetate, having the same concentration (in solution) of [BM$_2$Im][PF$_6$] as the first, at a mass ratio of 7.5:1; and the third prepared with the same concentration of cellulose acetate (in solution) as in the composite, but without any [BM$_2$Im][PF$_6$].

We evaluated the chemical-sensing properties of the novel films using a QCM transducer. Thin films were deposited on the gold electrode surface of the quartz crystal resonator, and we then measured the frequency and resistance responses of the sensor upon exposure to various VOCs. FIG. 3(a) depicts the frequency shift as a function of acetonitrile vapor concentrations for three different coatings: the first prepared using [BM$_2$Im][PF$_6$] only; the second one being a composite with cellulose acetate, having the same concentration (in solution) of [BM$_2$Im][PF$_6$] as the first, at a mass ratio of 7.5:1; and the third prepared with the same concentration of cellulose acetate (in solution) as in the composite, but without any [BM$_2$Im][PF$_6$]. The approximate mass loads calculated from the Sauerbrey equation (Eqn. 1) were 139 µg/cm$^2$ for [BM$_2$Im][PF$_6$], 176 µg/cm$^2$ for [BM$_2$Im][PF$_6$]/CA, and 3 µg/cm$^2$ for CA alone. For the [BM$_2$Im][PF$_6$]-only film, $\Delta f$ was substantially smaller in magnitude, and decreased at higher concentrations of acetonitrile. In other words, above a certain vapor concentration, the observed frequency increased with further increases in the vapor concentration. Similar non-Sauerbrey behavior has been observed by others during CO$_2$ absorption onto sugar acetate film, where it has been ascribed to deliquescence; and following moisture adsorption onto ZnO nanowire and ZnS nanowire films, where it was attributed to a decrease in the mechanical stiffness of the films. In marked contrast, as seen in FIG. 3(a) the [BM$_2$Im][PF$_6$]/CA film showed excellent linearity over a wide range of concentrations. Attempts were made to coat only CA using a similar procedure; however, a comparatively low mass loading resulted, one that produced a negligible frequency response. Note that this response was one that would still have been very low even if it had been linearly normalized to the amount of cellulose acetate in the composite.

Figure 3B:
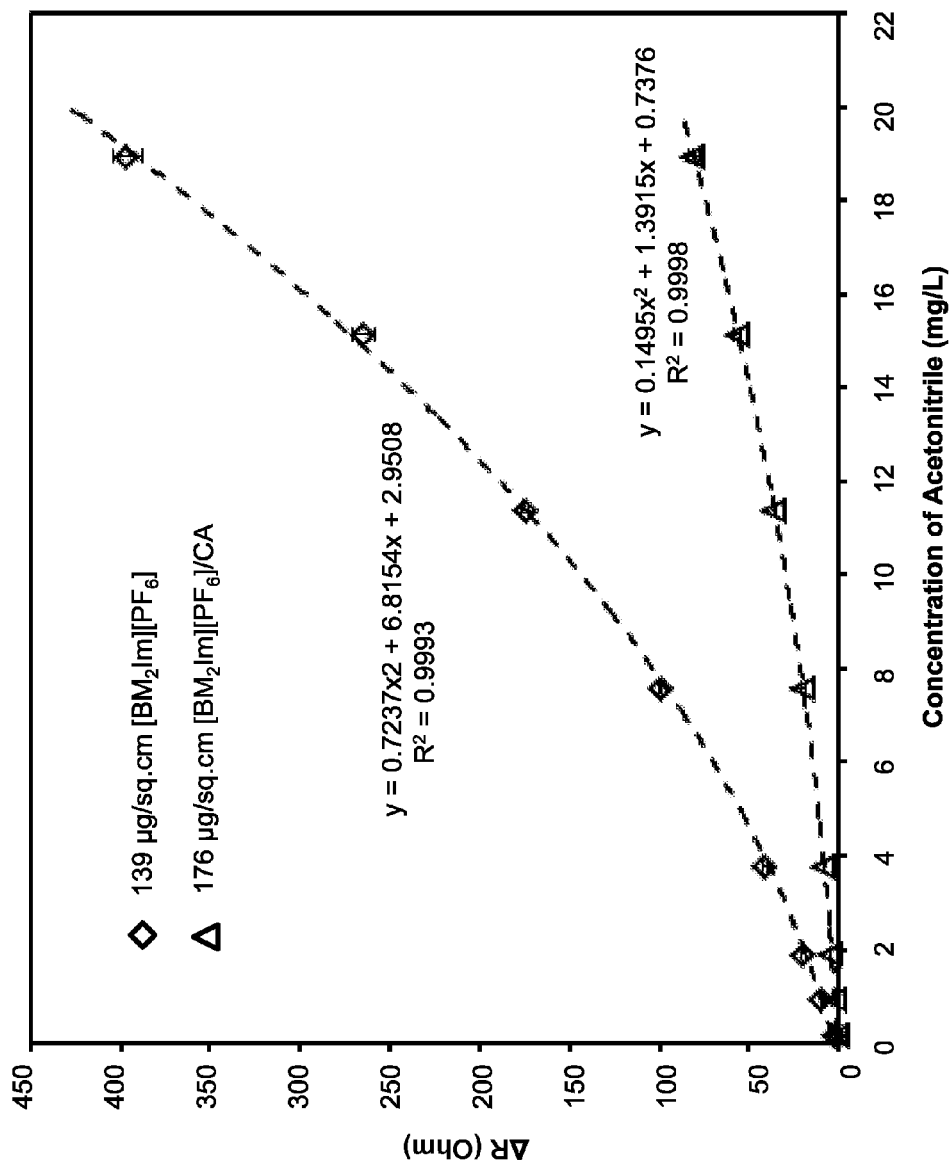
FIG. 3(b) depicts $\Delta R$ at different concentrations of acetonitrile for [BM$_2$Im][PF$_6$] and [BM$_2$Im][PF$_6$]/CA films.
Figure 3C:
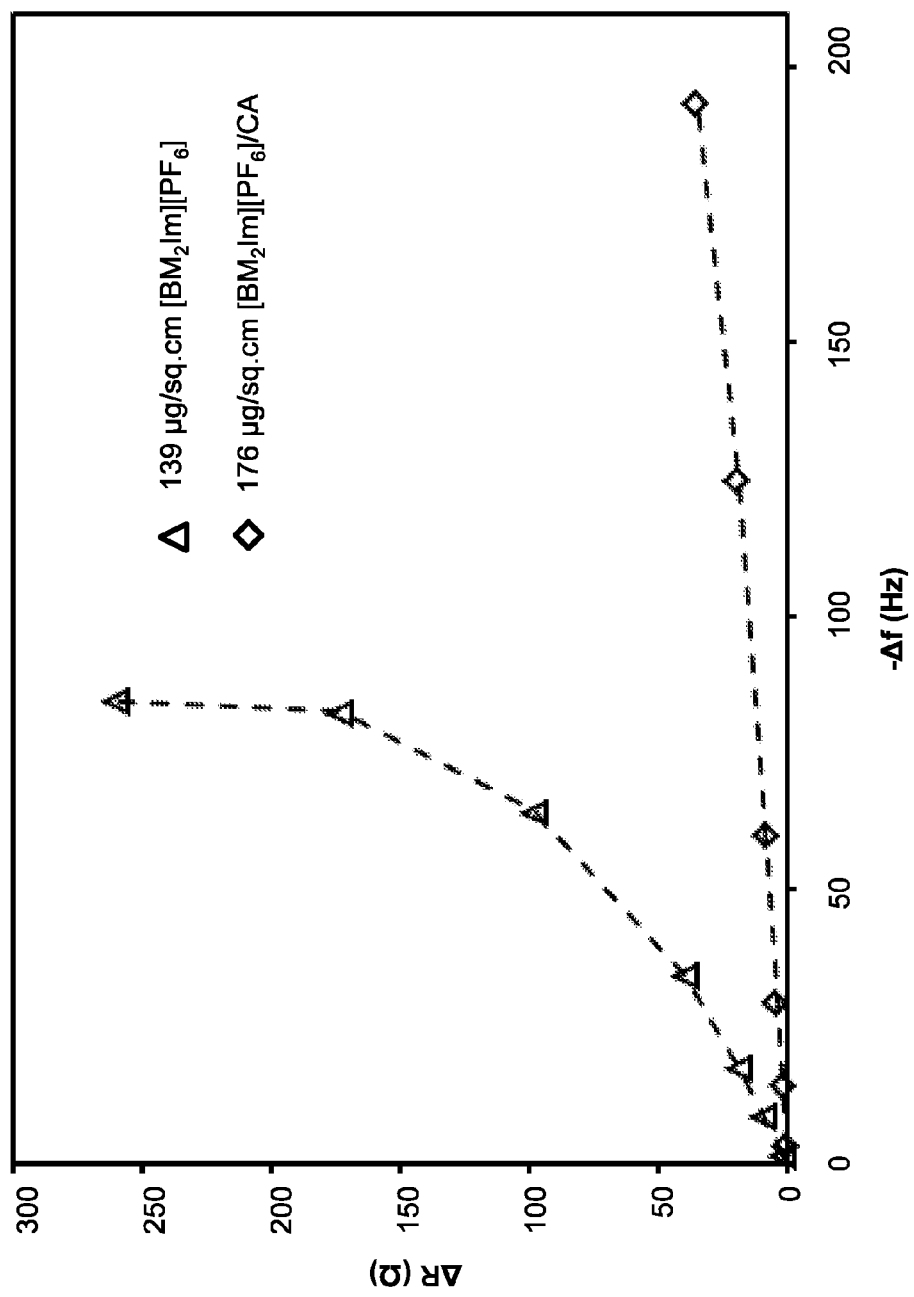
FIG. 3c depicts plots of motional resistance shift versus frequency change for [BM$_2$Im][PF$_6$] and [BM$_2$Im][PF$_6$]/CA films on exposure to varying concentrations of acetonitrile.

To better understand the reasons for enhanced performance of the [BM$_2$Im][PF$_6$]/CA film, we simultaneously measured $\Delta f$ and $\Delta R$ for both [BM$_2$Im][PF$_6$] and [BM$_2$Im][PF$_6$]/CA films upon sorption of acetonitrile vapors. As shown in FIG. 3b in both cases $\Delta R$ increased as a function of acetonitrile concentration. FIG. 3c depicts a plot of motional resistance shift versus frequency change for [BM$_2$Im][PF$_6$] and [BM$_2$Im][PF$_6$]/CA films on exposure to varying concentrations of acetonitrile. However, as shown in FIG. 3c the ratio $\Delta R/\Delta f$ was much higher for [BM$_2$Im][PF$_6$] than that for the [BM$_2$Im][PF$_6$]/CA film. The data in FIG. 3c imply that the [BM$_2$Im][PF$_6$]/CA film was substantially more rigid than the [BM$_2$Im][PF$_6$] film. (In each of FIGS. 3a, 3b, and 3c, the legends indicate the mass of film material on the QCR surface, in µg/cm$^2$.)

Example 13. Results of Molecular Dynamics Modeling

Our MD simulations showed that acetonitrile had negligible electrostatic and van der Waals interactions with CA. By contrast, stronger interactions occurred between acetonitrile and the [BM₂Im]⁺ and [PF₆]⁻ ions (data not shown). Similar trends were also seen in the simulations for other analytes (data not shown). Taken in aggregate, these observations implied that the sorption characteristics of the composite film were primarily attributable to [BM$_2$Im][PF$_6$], while the CA played an important role in improving the mechanical stiffness of the material. This increase in rigidity can be qualitatively rationalized using the simple 'rule-of-mixtures,' which is often used to estimate the mechanical response of a composite material from the properties and concentrations of its individual constituents. Our data led us to conclude that the [BM$_2$Im][PF$_6$]/CA composite film (7.5:1 mass ratio) is preferred for QCM-based vapor sensing. This preferred composite was used in testing various sensing applications of the film.

Example 14. Effects of Mass of Composite Material on Sensitivity

The sensitivity of the sensor (the change in the sensor's resonance frequency per unit change in analyte concentration) was observed to increase linearly with the amount of sensing material loaded onto the surface of the resonator (i.e., the mass per unit area; data not shown). The linear relationship between frequency shift and vapor concentration, and the linear relationship between the sensitivity and amount of sensing material indicated that the mass transfer process at the interface was predominantly the bulk absorption of vapors by the coating material. The mass of the sensing material deposited onto the resonator was controlled by changing the concentrations of [BM$_2$Im][PF$_6$] and CA (at a constant mass ratio), while holding the volumes of solvent and non-solvent constant. The maximum amount we loaded in this set of experiments was approximately 214 μg of the composite material per cm² of the electrode surface. While it would be possible to increase the mass loading further using the same coating procedure, higher mass loadings slowed the response, are thought to be less preferred, and were not studied in detail.

In marked contrast to the linear responses we observed using the novel GUMBOS composites, it has been reported that for RTILs, the sensitivity plateaus or the frequency change even becomes positive when the thickness of the coating exceeds ~200 nm, corresponding to a mass load of ~20-25 μg/cm². See, e.g., X. X. Jin, L. Yu, D. Garcia, R. X. Ren, X. Q. Zeng, *Anal. Chem.* 2006, 78, 6980; and X. M. Xu, H. W. Cang, C. Z. Li, Z. B. K. Zhao, H. Y. Li, *Talanta* 2009, 78, 711.

In a limited set of experiments, we have also tested RTILs in otherwise similar composites, and have not seen similar results to those we obtained with GUMBOS-based composites (data not shown). Without wishing to be bound by this hypothesis, we believe that the differences are due to the better ability of GUMBOS than RTILs to make gel-like composites with appropriate properties.

Examples 15-20. Response of Prototype Sensor Towards Six Gaseous Analytes

Figure 4:
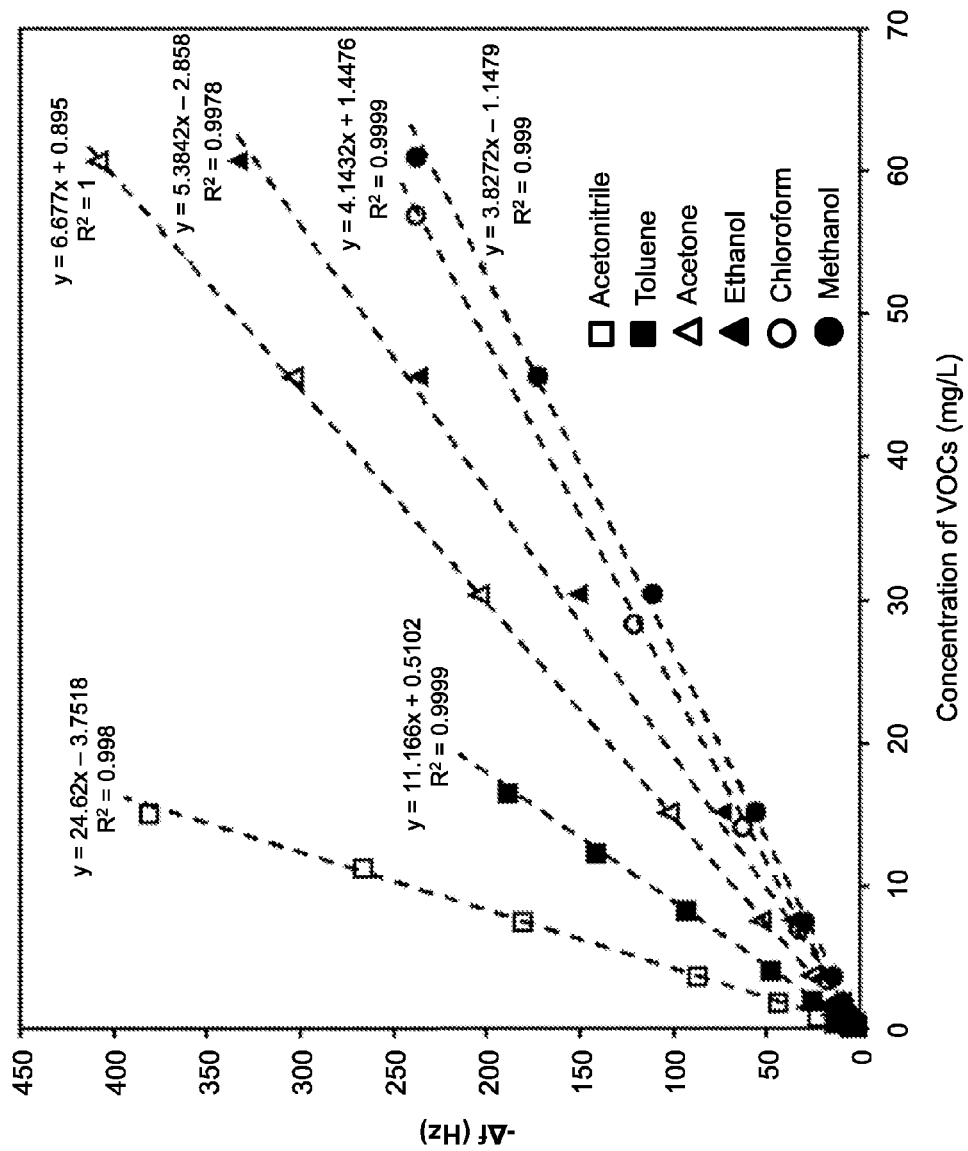
FIG. 4 depicts a plot of the frequency shift as a function of vapor concentration for each of six VOCs.

We investigated the response of the novel GUMBOS composite-coated QCM sensor towards six gaseous analytes: acetonitrile, acetone, chloroform, methanol, ethanol, and toluene. FIG. 4 depicts a plot of the frequency shift as a function of vapor concentration for each of the six VOCs. The sensor provided excellent linearity over a wide range of concentrations, as well as varying sensitivity to these chemically different organic vapors. The sensitivities, detection limits, and ranges studied are summarized in Table 1.

TABLE 1

Detection limits, sensitivities, and ranges studied for different VOCs

| VOC | Detection limit (mg/L) | Range studied (mg/L) | Sensitivity (Hz · L/mg) |
|---|---|---|---|
| acetone | 0.0806 | 0.19-60.8 | 6.7 |
| acetonitrile | 0.0267 | 0.19-15.2 | 24.6 |
| chloroform | 0.1271 | 0.36-57.0 | 4.1 |
| ethanol | 0.1189 | 0.19-60.8 | 5.4 |
| methanol | 0.1611 | 0.19-61.1 | 3.8 |
| toluene | 0.0508 | 0.21-16.7 | 11.2 |

Example 21. Enhancing the Sensitivity and Selectivity

The sensitivity can be further enhanced by using a higher frequency quartz resonator. In the Sauerbrey equation, the frequency shift is proportional to the square of the intrinsic frequency of the resonator. The sensitivity and selectivity can also be enhanced by employing different GUMBOS, with different chemical properties. A major factor influencing the sensitivity is the interaction energy between the analyte and the sorbent phase. Our MD simulations showed that the total interaction energy (electrostatic+van der Waals) experienced by a molecule differs from one analyte to another. The MD simulations predicted that the order of the analyte-sorbent interaction energies for the six analytes initially tested with the prototype [BM$_2$Im][PF$_6$]/CA composite film should be: acetonitrile>toluene>acetone>ethanol>methanol>chloroform. The predicted ordering correlated closely with the ordering of the experimental slopes seen in FIG. 4. Interaction energies were expressed in units of kJ/mol, while the slopes had units of Hz/(mg/L). For comparison, the measured values of the slopes were converted to moles of analyte absorbed per cm² for the same molar concentration of each vapor. Since Δf/(mg/L) is proportional to (moles/cm²)/(moles/L), the relative ordering remained the same.

Example 22. Other Sensor Characteristics

A rapid and reversible response that is consistent over time and after repeated exposures to analytes is a basic requirement for a viable sensor. FIG. 5 shows that the prototype sensor provided a stable baseline, and exhibited complete regeneration after repeated exposure to chloroform vapors. (The other five compounds studied showed similar behavior—data not shown.) FIG. 5 depicts the frequency and resistance responses of the sensor to four different concentrations of chloroform vapor over a course of time: (a) 17.8 mg/L, (b) 35.6 mg/L, (c) 53.4 mg/L, and (d) 71.3 mg/L. The upper curve depicts motional resistance, and the lower curve depicts frequency. In each case, a liquid sample was injected into the chamber and allowed to vaporize. After equilibrium, the vapor was removed by flushing with ultra-high purity argon. The amount of coating material on the QCR was 207 μg/cm².

The frequency baseline drift, which is normally a positive shift, was found to be minimal. The system was considered to be in equilibrium when the drift held at less than ±2 Hz/hr. The noise level was below 0.2 Hz, and hence the minimum detectable signal (3×noise) was 0.6 Hz. As compared to values previously reported for an RTIL-based QCM sensor, the detection limit was improved 46-fold for acetonitrile, 8.9-fold for methanol, and 8.1-fold for toluene. See I. Goubaidoulline, G. Vidrich, D. Johannsmann, *Anal. Chem.* 2005, 77, 615.

Figure 8:
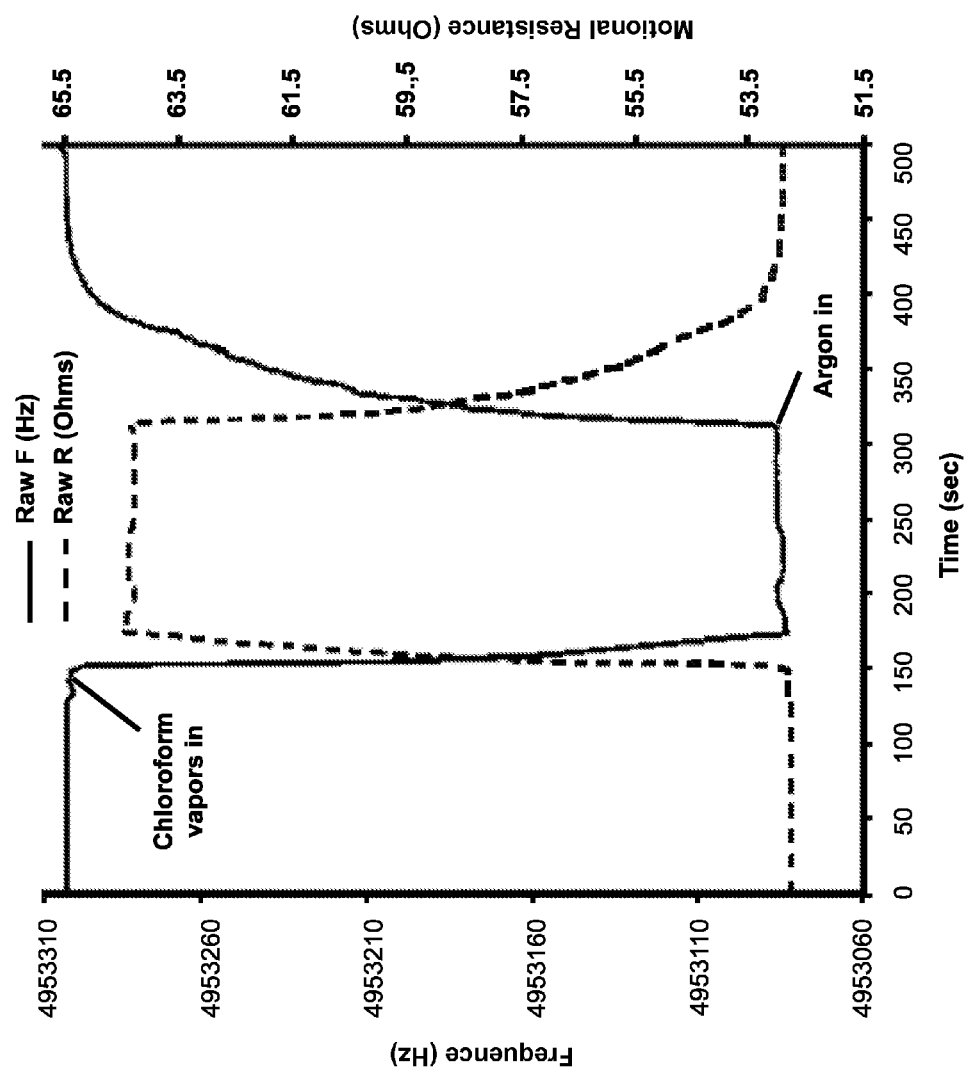
FIG. 8 depicts Δf, ΔR, response time, and regeneration time for chloroform vapor.

In order to estimate the response time, defined as the time to reach 99% of the stable value of the signal, chloroform vapors were introduced into the measuring chamber. A very short analytical response time was achieved, evidently less than one minute. See FIG. 8. However, precise measurement of the response time was not possible in these experiments due to complications introduced into the measurements by the time needed to fill the sample chamber. The regeneration time was apparently somewhat slower than the response time, but was also fast. Measurement of the regeneration time was likewise complicated by the time needed for analyte vapor to clear from the chamber.

Example 23. Potential Applications in Sensor Arrays

A typical "real-world" sample contains a mixture of different volatile organic compounds. Creating a single sensor that is capable of accurately discriminating a single compound from a complex mixture is a substantial challenge. An alternative approach is to employ a sensor array rather than a single sensor. A sensor array is a group of complementary sensors that use pattern recognition or similar techniques for the identification or quantification of multiple analytes. Array-based detection systems do not require highly specific sensors. However, in general the various sensor elements should exhibit different responses to different analytes. The chemical sensitivity of a sensor material can be modulated by a change in its chemical structure. Since chemically diverse GUMBOS may readily be synthesized by simply modifying or changing the cationic and/or anionic components of the molecule, these compounds are well-suited for array-based gas sensing applications.

Figure 6A:
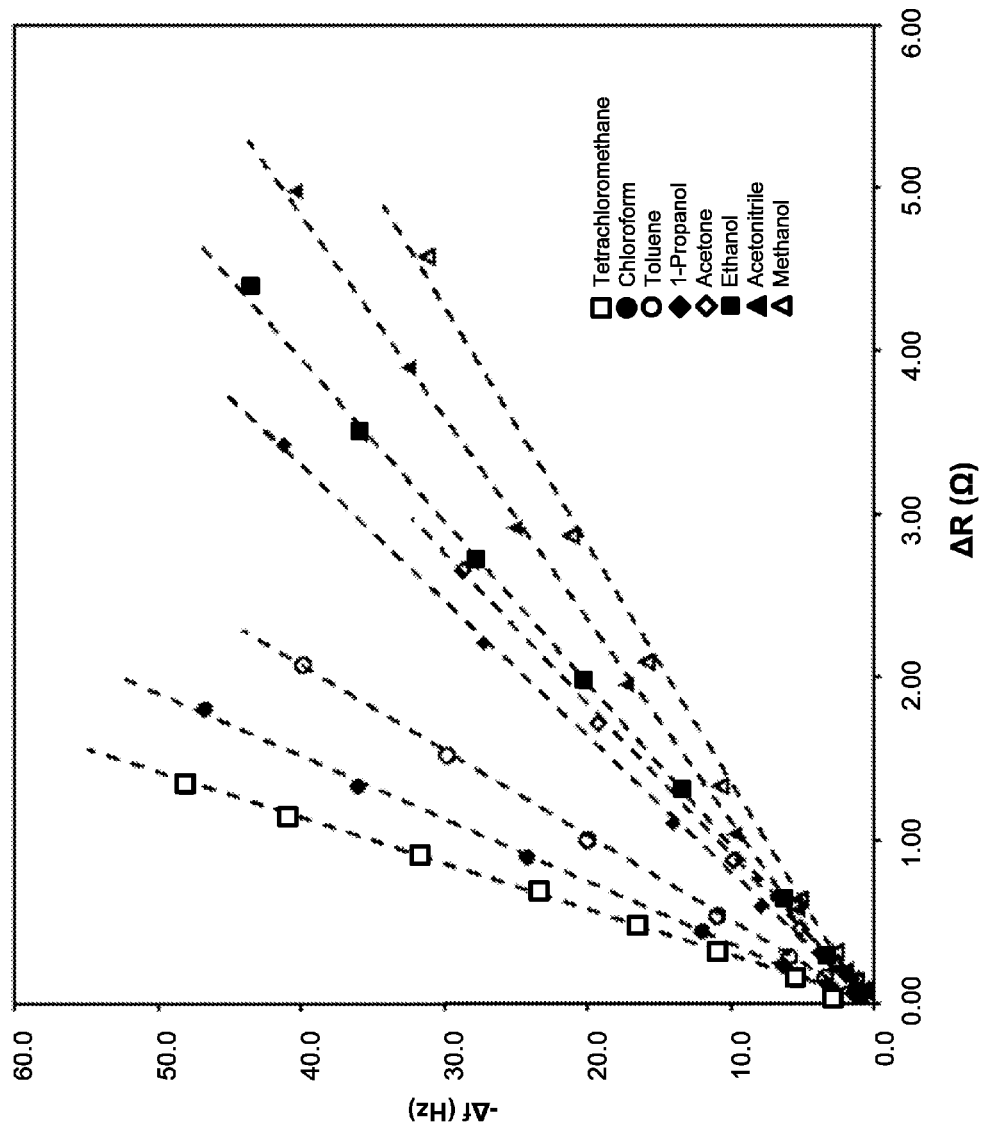
FIG. 6(a) depicts a plot of Δf versus ΔR for eight VOCs. The amount of coating material was 83 μg of composite film per cm$^2$ of electrode area.
Figure 6B:
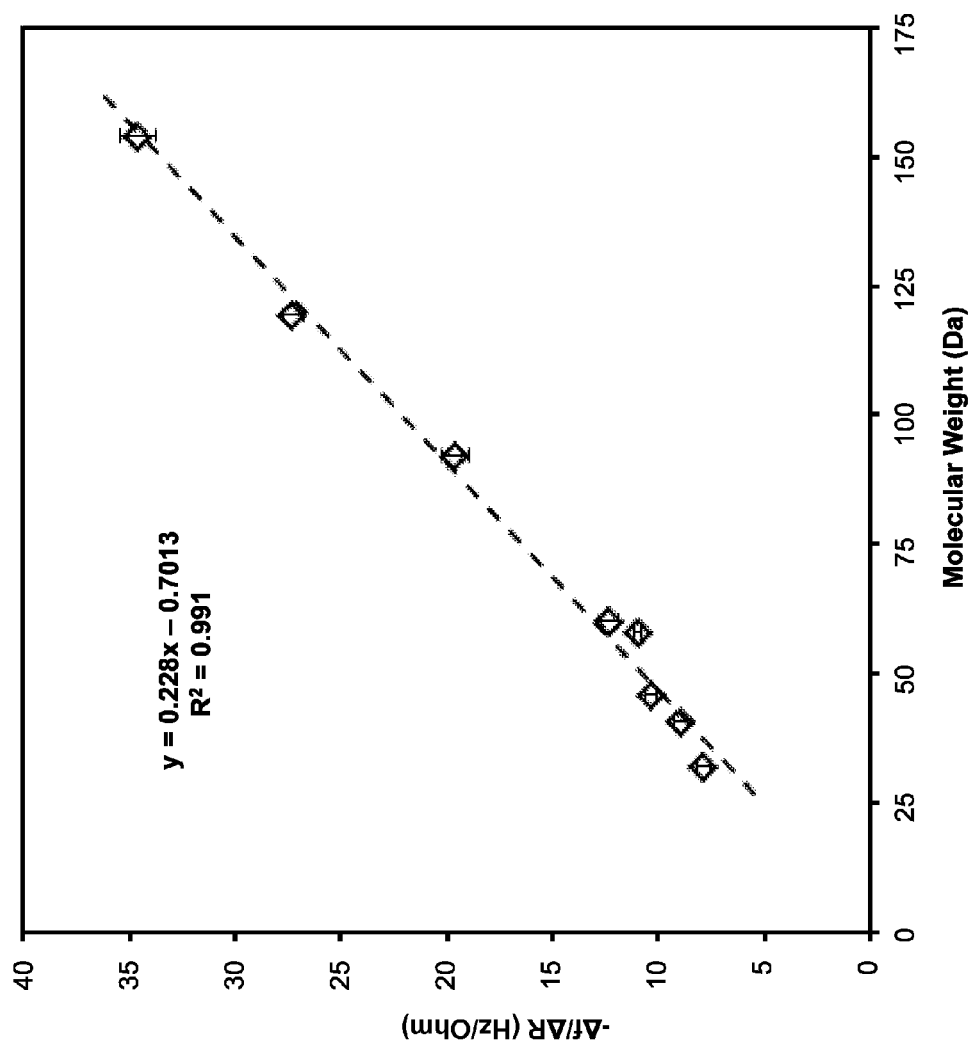
FIG. 6(b) depicts a plot of the ratio Δf/ΔR versus molecular weight for each of the eight compounds using the same film as in FIG. 6(a).
Figure 9:
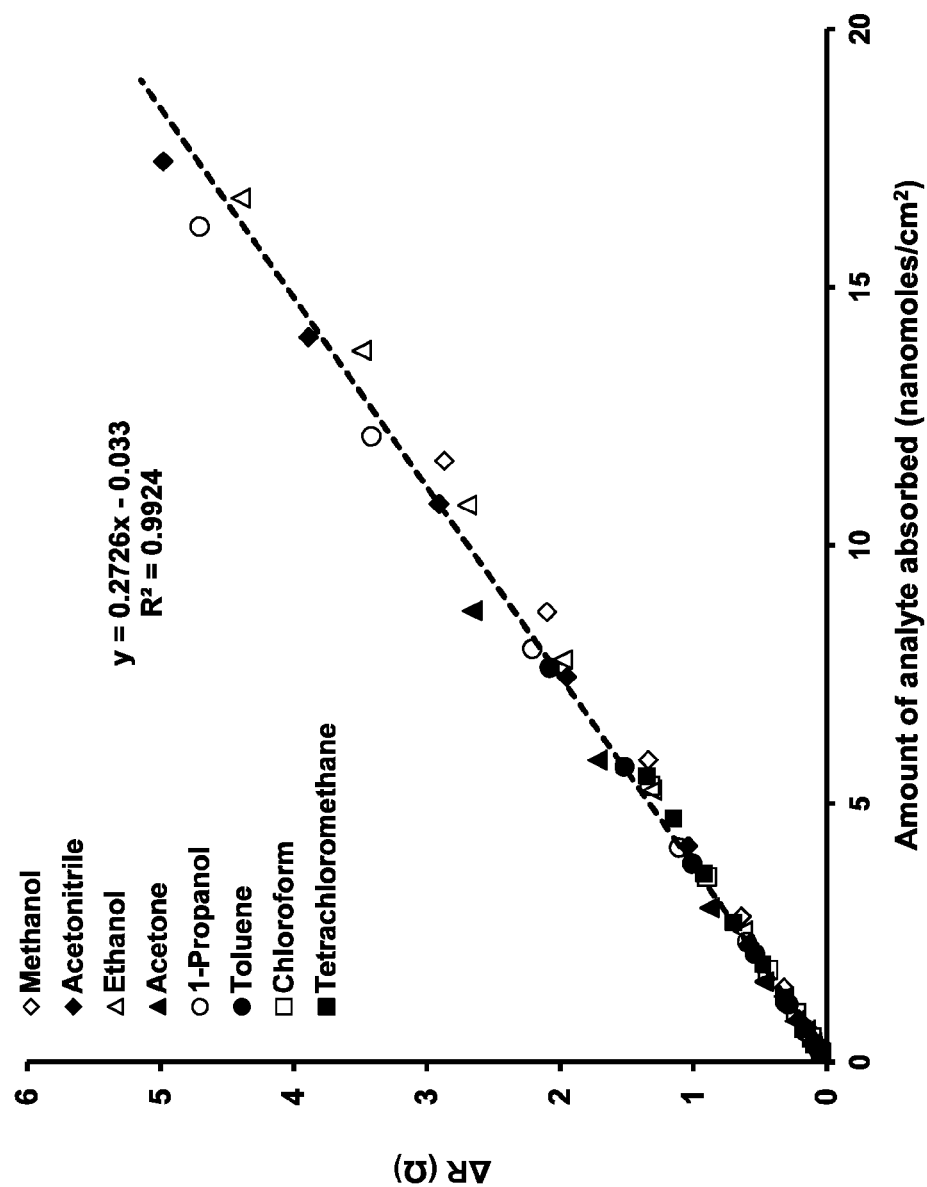
FIG. 9 depicts, for the same data given in FIG. 6(a), a plot of ΔR versus nanomoles of compound absorbed per square centimeter.

Example 24. Determination of Molecular Weight, and Discrimination Between Different Compounds The composite-coated QCM can be used for molecular weight determination and discrimination of organic vapors. FIG. 5 showed that the motional resistance shift and the frequency shift were rapid, stable, and reversible. We have simultaneously measured $\Delta f$ and $\Delta R$ for our prototype QCM sensor upon exposure to each of the six compounds studied above, as well as two additional analytes: 1-propanol, and tetrachloromethane. The analytes included both polar and non-polar compounds. FIG. 6(*a*) depicts a plot of $\Delta f$ versus $\Delta R$ for each of these eight compounds. The plots were linear over a wide range of vapor concentrations for each compound. The data presented in FIG. 6(*a*) were obtained under intermediate loading conditions for the composite: 83 µg of composite film per cm² of electrode area. The analyte concentration ranges were: 1.93-77.0 mg/L for tetrachloromethane, 0.720-28.8 mg/L for chloroform, 0.209-8.36 mg/L for toluene, 0.194-11.7 mg/L for 1-propanol, 0.191-11.5 mg/L for acetone, 0.382-22.9 mg/L for ethanol, 0.190-4.75 mg/L for acetonitrile, and 0.574-23.0 mg/L for methanol. FIG. 9 depicts, for the same data given in FIG. 6(*a*), a plot of $\Delta R$ versus nanomoles of compound absorbed per square centimeter. Note in particular in FIG. 9 that $\Delta R$ was directly proportional to the number of moles of analyte absorbed for a variety of different VOCs, regardless of the chemical nature of the individual compounds.

FIG. 6(*b*) depicts a plot of the ratio $\Delta f/\Delta R$ versus molecular weight for each of the eight compounds. These data points were obtained by taking the ratio of $\Delta f/\Delta R$ at 6-8 different vapor concentrations within the ranges shown in FIG. 6(*a*). This plot showed excellent linearity between $\Delta f/\Delta R$ and the molecular weight of the analytes, as demonstrated by the high correlation coefficient ($r^2>0.99$). Error bars are included in FIG. 6(*b*), but the magnitude of the standard deviations was so small that the error bars may be difficult to see. A slight deviation from linearity was consistently observed for acetone (M.W. 58), possibly due to water vapor in the sample. The relationship between $\Delta f/\Delta R$ and molecular weight can be expressed by the following equation:

$$\frac{\Delta f}{\Delta R} = k \times M.W. + C \qquad \text{(Equation 2)}$$

where k and C are constants, and M. W. is the molecular weight of the absorbed species. From our data, C appeared to be equal to zero, within experimental error, leading to the simpler form:

$$\frac{\Delta f}{\Delta R} = k \times M.W. \qquad \text{(Equation 2a)}$$

To the inventors' knowledge, a linear dependence between $\Delta f$ and $\Delta R$ for a given compound has not been previously reported. Nor has a linear dependence between the ratio $\Delta f/\Delta R$ and the molecular weight across a range of different compounds been previously reported. The simultaneous measurement of $\Delta f$ and $\Delta R$ can thus be used to determine the molecular weights of compounds, and to help discriminate between different vapor molecules, irrespective of their concentrations. Note that the measurement of either $\Delta f$ alone or $\Delta R$ alone would not provide the molecular identity, because the response depends upon both the concentration and the identity of the chemical species.

Example 25. Theoretical Basis for Sensor Behavior

Without wishing to be bound by the hypotheses given here, the inventors propose the following theoretical explanation for the behavior and properties of the novel sensors. We explain our observations using concepts of free volume and viscoelasticity. According to free-volume theory, the unoccupied space (free volume) in solids and liquids contains both "interstitial" free volume and "hole" free volume (i.e., that for holes or vacancies). Another assumption of this theory is that the interstitial free volume is uniformly distributed, while holes or vacancies are discontinuously distributed throughout the material. It is the "hole" free volume that is primarily responsible for molecular transport. This theory has previously been applied primarily to polymers. However, the responses are likely to be different for GUMBOS composites and polymers due to their structural differences.

G. Dlubek, Y. Yu, R. Krause-Rehberg, W. Beichel, S. Bulut, N. Pogodina, I. Krossing, C. Friedrich, *J. Chem. Phys.* 2010, 133, 124502 recently demonstrated the presence of subnanometer-size holes both in the solid and liquid states of ILs using positron annihilation lifetime spectroscopy.

These holes are comparable in size to the size of the constituting ions. The estimated hole density was $2.0 \times 10^{20}$ g$^{-1}$. The solubility and diffusion of gases in ILs have been explained using the concept of 'free volume' or 'void space' available in these materials. The rapid response and recovery times observed for the novel sensor can be attributed to the presence of free volumes that facilitate the rapid diffusion of analyte molecules within the films.

Another aspect to consider is the viscoelastic behavior of ILs. W. Makino, R. Kishikawa, M. Mizoshiri, S. Takeda, M. Yao, *J. Chem. Phys.* 2008, 129, 104510 demonstrated that alkyl imidazolium-based ILs having sufficiently long side chains (≥C4) exhibit viscoelastic properties. We attribute the observed motional resistance change for our composites to the viscoelastic properties of these films. For viscoelastic materials, the shear modulus (G) can be represented as a complex quantity: $G=G'+jG''$, where G' is shear storage modulus of the film, G'' is the shear loss modulus of the film, and j denotes the imaginary unit $\sqrt{-1}$. A review of the literature indicates that motional resistance depends upon the following film parameters: shear modulus, thickness, mass density, and particle surface coverage. The viscoelastic properties of polymer films have been extensively studied. For polymers, substantial changes in both G' and G'' have been observed during vapor absorption. The shear modulus is the more important parameter determining changes in motional resistance. For polymers it is known that vapor absorption induces film swelling, leading to an increase in free volume, a decrease in shear modulus, increased viscoelastic damping, and increased motional resistance. Our data with the novel GUMBOS composites showed that the observed frequency shift was directly proportional to the vapor phase concentration of the analytes (See, e.g., FIG. 4). The concentration of a compound in the sorbent phase, Cs, may be related to the concentration of the compound in the vapor phase, $C_v$, through a partition constant K:

$$K=C_s/C_v \qquad \text{(Equation 3)}$$

Equation 3, together with data such as shown in FIG. 4 imply that Δf is directly proportional to the mass of the compound absorbed into the film. This conclusion is consistent with the Sauerbrey equation. Equation 2 then implies that any motional resistance increase is directly proportional to the number of molecules of analyte absorbed, and that it is largely independent of the chemical properties of the molecules. See FIG. 9. This is believed to represent a novel discovery, never previously reported.

A simple theoretical analysis accounts, at least qualitatively, for our experimental observations. We assume that motional resistance increase is due to changes in mass density, thickness, and shear modulus of the film, since these are the only parameters that should change during vapor absorption. Because the amount of vapor absorbed is relatively low (the estimated maximum mass fraction of analyte in our experiments was about 0.01), the density of the sorbent-analyte system remained essentially the same for all analytes, given an equal number of absorbed molecules. Our MD simulations indicated that the total interaction energy between an analyte molecule and other species present in the system (e.g., [BM$_2$Im]$^+$, [PF$_6$]$^-$ and CA), was much lower than the total interaction energy experienced by a typical cation, anion, or oligomer of CA in the same system. The MD results suggested that the VOC molecules did not interact appreciably with the species in the sorbent matrix. Because the analyte is present in low concentrations and does not interact strongly with the sorbent phase, it is possible that the vapor molecules behave more-or-less as an ideal gas within the free volume of the sorbent matrix. Consequently, the same number of molecules of analyte should produce similar thickness changes and free volume changes, and should be more-or-less independent of the chemical identity of the analyte molecules. To a good approximation, the motional resistance increase depends only on the number of molecules that are absorbed. The free volume increase occurs primarily through hole expansion and new hole formation.

Examples 26-28. Preliminary Experimental Studies Using Other GUMBOS

We have also performed preliminary vapor sensing studies using three other GUMBOS: 1-n-butyl-2,3-dimethylimidazolium trifluoromethanesulfonate ([BM$_2$Im][OTf]); 1-n-butyl-3-methylpyridinium hexafluorophosphate ([BMPyr][PF$_6$]); and 1-ethyl-2,3-dimethylimidazolium hexafluorophosphate ([EM$_2$Im][PF$_6$]). [BM$_2$Im][OTf] and [BMPyr][PF$_6$] showed similar behavior to that of [BM$_2$Im][PF$_6$]. By contrast, [EM$_2$Im][PF$_6$] exhibited decreased sensitivity, very slow response, and negligible resistance changes. These observations supported our contention that free volume and viscoelasticity play an important role in determining the unique response observed for our sensor. We believe that [EM$_2$Im][PF$_6$] does not show appreciable viscoelastic behavior and has less free volume due to a decrease in the length of the alkyl side chain. We have also used another derivative of cellulose, cellulose acetate butyrate, with similar observations.

Properties that are desirable for the GUMBOS used in this invention include: chemical stability, thermal stability, good glass transition temperature, and amphiphilicity—the ability to dissolve both hydrophobic and hydrophilic VOCs. Undesirable properties include: low stability, reactivity with VOCs (irreversible sorption), hygroscopicity. Coating stability is most likely enhanced by forming a composite with a matrix material such as cellulose acetate.

Example 29. Other GUMBOS that May be Used in this Invention

Ionic liquids typically comprise relatively bulky organic cations and diffuse-charge inorganic anions such as PF$_6^-$, BF$_4^-$, Tf$_2$N$^-$, or NO$_3^-$, although in some ILs the anion is organic, or both cation and anion may be organic. Typically, the ions are sterically mismatched, hindering crystal formation. The properties of ILs are highly "tunable," allowing ready modifications to meet specific needs by simple changes in the cation, the anion, or both. In addition, many ILs have useful properties such as high thermal stability, non-flammability, and essentially zero vapor pressure.

"Frozen" IL nanoparticles have distinct properties from other types of nanoparticles. ILs are broadly tunable by modifying the anionic constituents, the cationic constituents, or both; meaning that many properties may readily be altered, such as melting point, density, viscosity, surface tension, solubility, tensile strength, hydrophobicity, hydrophilicity, rigidity, reactivity, radioactivity, magnetic properties, optical properties, and other physical and chemical properties. Some examples of high-melting-temperature ("frozen") ILs are given in Tables 2 and 3 below, and other examples are known in the art. GUMBOS have a melting point between 25° C. and 250° C.

TABLE 2

Examples of Ionic Liquids with melting points 25-100° C.

| | Example | MP (° C.) |
|---|---|---|
| Imidazolium-Based | 1,3-Dimethylimidazolium trifluoromethanesulfonate | 43 |
| | 1-Ethyl-3-methylimidazolium chloride | 88 |
| | 1-Ethyl-3-methylimidazolium bromide | 65 |
| | 1-Butyl-3-methylimidazolium chloride | 73 |
| | 1-Ethyl-3-methylimidazolium tosylate | 56 |
| Pyridinium-Based | N-Butyl-3,4-dimethylpyridinium chloride | 72 |
| | N-Butyl-4-methylpyridinium hexafluorophosphate | 44 |
| | N-Butylpyridinium hexafluorophosphate | 75 |
| Ammonium-based | Methyltrioctylammonium triflate | 56 |
| | Tetraethylammonium tris (pentafluoroethyl)trifluorophosphate | 97 |
| | Tetrabutylammonium bis(trifluoromethylsulfonyl)imide | 92 |
| Pyrrolidinium-based | 1-Butyl-1-methylpyrrolidinium bis[oxalato(2-)] bromide | 55 |
| | 1-Butyl-1-methylpyrrolidinium trifluoroacetate | 31 |
| | 1-Butyl-1-methylpyrrolidinium hexafluorophosphate | 85 |
| Phosphonium-Based | Trihexyltetradecylphosphonium tetrafluoroborate | 25 |
| Amino acid-based | Tetrabutyl ammonium alanate | 76 |
| | Alanine methyl ester lactate | 38 |
| | Alanine butyl ester tetrafluoroborate | |
| Fluorescent and absorption dye-based | Rhodamine B bis (trifluoromethane) sulfonimide | 80 |
| | CrystViolet hexafluorophosphate | 60 |
| | BasicYellow hexafluorophosphate | 85 |
| | Methylviolet2B bis (trifluoromethane) sulfonimide | 48 |
| | MalachiteGreen hexafluorophosphate | 60 |
| Near infra-red dyes | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium bis(pentafluoroethylsulfonyl)imide | 52 |
| | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium tetraphenyl borate | 87 |
| | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium 3,5-bis(trifluoromethyl)phenyltrifluoroborate | 82 |
| | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium 4-(trifluoromethyl)phenyltrifluoroborate | 80 |
| | 1,3,3-Trimethyl-2-[7-(1,3,3-trimethyl-1,3-dihydro-indol-2-ylidene)-hepta-1,3,5-trienyl]-3H-indolium tetraphenyl borate | 98 |
| | 1,3,3-Trimethyl-2-[7-(1,3,3-trimethyl-1,3-dihydro-indol-2-ylidene)-hepta-1,3,5-trienyl]-3H-indolium 4-(trifluoromethyl)phenyltrifluoroborate | 99 |
| | 1,3,3-Trimethyl-2-[7-(1,3,3-trimethyl-1,3-dihydro-indol-2-ylidene)-hepta-1,3,5-trienyl]-3H-indolium tetrakis[3,5-bis(1,1,1,3,3,3-hexafluoro-2-methoxy-2-propyl)phenyl]borate | 72 |
| | 2-(2-{2-Chloro-3-[2-(1,3,3-trimethyl-1,3-dihydro-indol-2-ylidene)-ethylidene]-cyclohex-1-enyl}-vinyl)-1,3,3-trimethyl-3H-indolium bis (trifluoromethane) sulfonimide | 89 |
| | 2-[2-[2-Chloro-3-[2-(1,3-dihydro-1,3,3-trimethyl-2H-indol-2-ylidene)-ethylidene]-1-cyclopenten-1-yl-ethenyl]-1,3,3-trimethyl-3H-indolium hexafluorophosphate | 85 |
| Vitamin-based | Vitamin B4 lactate | 100 |
| | Nicotinamide adenine dinucleotide lactate | 40 |
| | Riboflavin 5'-adenosine diphosphate lactate | 40 |
| Anti-bacterial/viral compound-based | Amantadine bis (trifluoromethane) sulfonimide | 95 |

See generally also: (1) the Ionic Liquid Data Bank, NIST Standard Reference Database #147, currently available online at ilthermo.boulder.nist.gov; (2) H. Ohno et al., Accounts of Chemical Research. 2007, 40, 1122; and (3) M. Patil et al., Tetrahedron. 2007, 63, 12702.

TABLE 3

Examples of Ionic Liquids with melting points 100-200° C.

| | Example | MP(° C.) |
|---|---|---|
| Imidazolium-based | 1-Dodecyl-3-methylimidazolium chloride | 134 |
| | 1-Ethyl-2,3-dimethylimidazolium bromide | 138 |
| | 1-Ethyl-2,3-dimethylimidazolium trifluoromethanesulfonate | 110 |
| Pyridinium-based | N-Butylpyridinium bromide | 105 |
| | N-Butyl-3-methylpyridinium chloride | 117 |
| | N-Ethylpyridinium chloride | 119 |
| Ammonium-based | Tetramethylammonium bis[oxalato(2-)] bromide | 130 |
| | Tetramethylammonium tris (pentafluoroethyl)trifluorophosphate | 115 |
| | Tetramethylammonium bis(trifluoromethanesulfonyl)imide | 135 |
| Pyrrolidinium-based | 1,1-Dimethylpyrrolidinium tris(pentafluoroethyl) trifluorophosphate | 107 |
| | 1-Butyl-1-methylpyrrolidinium tetrafluoroborate | 147 |
| Amino acid-based | Alanine butyl ester nitrate | 104 |
| | Alanine butyl ester lactate | 114 |
| Fluorescent dye-based | Rhodamine 6G nitrate | 126 |
| | CrystalViolet bis(trifluoromethanesulfonyl)imide | 170 |
| | Thioflav bis(trifluoromethanesulfonyl)imide | 169 |
| | BasicYellow bis(trifluoromethanesulfonyl)imide | 127 |
| Near infra-red dyes | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium bis(trifluoromethanesulfonyl)imide | >120 |
| | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium trifluorophenylborate | >120 |
| | 1,3,3-Trimethyl-2-[7-(1,3,3-trimethyl-1,3-dihydro-indol-2-ylidene)-hepta-1,3,5-trienyl]-3H-indolium bis(pentafluoroethylsulfonyl)imide | >120 |
| | 1,3,3-Trimethyl-2-[7-(1,3,3-trimethyl-1,3-dihydro-indol-2-ylidene)-hepta-1,3,5-trienyl]-3H-indolium bis(trifluoromethanesulfonyl)imide | >120 |

TABLE 3-continued

Examples of Ionic Liquids with melting points 100-200° C.

| | Example | MP(° C.) |
|---|---|---|
| | 1,3,3-Trimethyl-2-[7-(1,3,3-trimethyl-1,3-dihydro-indol-2-ylidene)-hepta-1,3,5-trienyl]-3H-indolium 3,5-bis(trifluoromethyl)phenyltrifluoroborate | >120 |
| | 1,3,3-Trimethyl-2-[7-(1,3,3-trimethyl-1,3-dihydro-indol-2-ylidene)-hepta-1,3,5-trienyl]-3H-indolium tetrafluoroborate | >120 |
| | 2-(2-{2-Chloro-3-[2-(1,3,3-trimethyl-1,3-dihydro-indol-2-ylidene)-ethylidene]-cyclohex-1-enyl}-vinyl)-1,3,3-trimethyl-3H-indolium bis(pentafluoroethylsulfonyl)imide | >100 |
| Vitamin-based | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium bis(trifluoromethanesulfonyl)imide | 140 |
| Anti-bacterial/viral compound-based | 1-Butyl-2-(2-{3-[2-(1-butyl-3,3-dimethyl-1,3-dihydro-indol-2-ylidene)-ethylidene]-2-chloro-cyclohex-1-enyl}-vinyl)-3,3-dimethyl-3H-indolium trifluorophenylborate | 180 |

Additional ionic liquids that might be used in one or more of the above applications include, for example: Rhod6G $NO_3$, CrystViol $NTf_2$, Thioflav $NTf_2$, BasicYellow $NTf_2$, $VitB_4$ $PF_6$ and Tetracycline $NTf_2$.

MISCELLANEOUS

As used in the specification and claims, unless context clearly indicates otherwise, an "ionic liquid" is a salt having a melting point below about 250° C.; and in many cases is below about 100° C., so that an aqueous solvent may be used in the synthesis. The term "ionic liquid" thus includes compositions that are, in fact, solids at temperatures below their respective melting points. The term does not imply that the salt is necessarily a liquid at any particular time; rather, it refers to the salt's melting point. Where an IL has a melting point above 100° C., higher boiling point solvents may be used such as glycerol, paraffin, mineral oil, and other solvents known in the art. Likewise, where a particular IL is water-soluble, then a nonaqueous solvent may be used for dispersal.

The melting point, according to the use for which the film is intended, may be chosen to greater than or equal to about: 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., or 245° C.

The melting point, according to the use for which the film is intended, may be chosen to less than or equal to about: 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., or 250° C.

An "organic salt" is a salt comprising at least one organic anion, or at least one organic cation, or both an organic anion and an organic cation. Examples of organic ions that may be used include, for example: tosylate, trifluoromethanesulfonate, tris(pentafluoroethyl)trifluorophosphate, bis(trifluoromethylsulfonyl)imide, lactate, tetraphenyl borate, 3,5-bis(trifluoromethyl)phenyltrifluoroborate, 4-(trifluoromethyl)phenyltrifluoroborate, tetrakis[3,5-bis(1,1,1,3,3,3-hexafluoro-2-methoxy-2-propyl)phenyl]borate, trifluorophenylborate, saccharin, acesulfame, fluorescein, eosin, and their respective derivatives.

The IL melting point is preferably higher than any temperatures at which the film will be used. In principle, there is no upper limit on what the melting point may be. As a practical matter, for many applications the melting point will be between about 25° C. and about 200° C. For convenience of handling and preparation, the melting point will often be between about 40° C. and about 100° C., a range that is appropriate for most of the applications discussed here.

REFERENCES

[1] E. S. Snow, F. K. Perkins, E. J. Houser, S. C. Badescu, T. L. Reinecke, *Science* 2005, 307, 1942.
[2] B. Li, G. Sauve, M. C. Iovu, M. Jeffries-El, R. Zhang, J. Cooper, S. Santhanam, L. Schultz, J. C. Revelli, A. G. Kusne, T. Kowalewski, J. L. Snyder, L. E. Weiss, G. K. Fedder, R. D. McCullough, D. N. Lambeth, *Nano Lett.* 2006, 6, 1598.
[3] P. Si, J. Mortensen, A. Kornolov, J. Denborg, P. J. Moller, *Anal. Chim. Acta* 2007, 597, 223.
[4] C. Di Natale, A. Macagnano, E. Martinelli, R. Paolesse, G. D'Arcangelo, C. Roscioni, A. Finazzi-Agro, A. D'Amico, *Biosens. Bioelectron.* 2003, 18, 1209.
[5] R. A. Miller, G. A. Eiceman, E. G. Nazarov, A. T. King, *Sens. Actuators, B* 2000, 67, 300.
[6] M. D. Krebs, A. M. Zapata, E. G. Nazarov, R. A. Miller, I. S. Costa, A. L. Sonenshein, C. E. Davis, *IEEE Sens. J.* 2005, 5, 696.
[7] M. Chai, J. Pawliszyn, *Environ. Sci. Technol.* 1995, 29, 693.
[8] H. Oser, M. J. Coggiola, S. E. Young, D. R. Crosley, V. Hafer, G. Grist, *Chemosphere* 2007, 67, 1701.
[9] J. D. Cuiffi, D. J. Hayes, S. J. Fonash, K. N. Brown, A. D. Jones, *Anal. Chem.* 2001, 73, 1292.
[10] A. K. Kalkan, M. R. Henry, H. D. Li, J. D. Cuiffi, D. J. Hayes, C. Palmer, S. J. Fonash, *Nanotechnology* 2005, 16, 1383.
[11] M. Maute, S. Raible, F. Prins, D. Kern, H. Ulmer, U. Weimar, W. Gˆpel, *Sens. Actuators, B* 1999, 58, 505.
[12] S. Maldonado, E. Garcia-Berrios, M. D. Woodka, B. S. Brunschwig, N. S. Lewis, *Sens. Actuators, B* 2008, 134, 521.
[13] M. E. Escuderos, S. Sanchez, A. Jimenez, *Food Chem.* 2011, 124, 857.
[14] G. Sauerbrey, *Z. Phys.* 1959, 155, 206.
[15] C. Dixon Matthew, *J. Biomol. Tech.* 2008, 19, 151.
[16] A. L. Smith, R. B. Mulligan, H. M. Shirazi, *J. Polym. Sci., Part B: Polym. Phys.* 2004, 42, 3893.
[17] V. L. Strashilov, G. E. Alexieva, V. N. Velichkov, R. P. Mateva, I. D. Avramov, *Sens. Lett.* 2009, 7, 203.
[18] H. Sugimoto, H. Tanaka, Y. Kanno, *Jpn. J. Appl. Phys.* 2008, 47, 637.
[19] B. C. Sisk, N. S. Lewis, *Langmuir* 2006, 22, 7928.
[20] L. Sartore, M. Penco, S. Della Sciucca, G. Borsarini, V. Ferrari, *Sens. Actuators, B* 2005, 111, 160.
[21] M. Consales, A. Cutolo, M. Penza, P. Aversa, G. Cassano, M. Giordano, A. Cusano, *IEEE T. Nanotechnol.* 2007, 6, 601.

[22] M. Penza, G. Cassano, P. Aversa, F. Antolini, A. Cusano, M. Consales, M. Giordano, L. Nicolais, *Sens. Actuators, B* 2005, 111, 171.

[23] R. Shinar, G. J. Liu, M. D. Porter, *Anal. Chem.* 2000, 72, 5981.

[24] N. Kasai, I. Sugimoto, M. Nakamura, T. Katoh, *Biosens. Bioelectron.* 1999, 14, 533.

[25] S. Arshad, M. M. Salleh, M. Yahaya, *Sens. Lett.* 2008, 6, 903.

[26] A. F. Holloway, A. Nabok, A. A. Hashim, J. Penders, *Sens. Transducers J.* 2010, 113, 71.

[27] I. A. Koshets, Z. I. Kazantseva, Y. M. Shirshov, S. A. Cherenok, V. I. Kalchenko, *Sens. Actuators, B* 2005, 106, 177.

[28] B. Wyszynski, P. Somboon, T. Nakamoto, *Sens. Actuators, B* 2008, 130, 857.

[29] C. D. Liang, C. Y. Yuan, R. J. Warmack, C. E. Barnes, S. Dai, *Anal. Chem.* 2002, 74, 2172.

[30] X. X. Jin, L. Yu, D. Garcia, R. X. Ren, X. Q. Zeng, *Anal. Chem.* 2006, 78, 6980.

[31] X. X. Jin, L. Yu, X. Q. Zeng, *Sens. Actuators, B* 2008, 133, 526.

[32] I. Goubaidoulline, G. Vidrich, D. Johannsmann, *Anal. Chem.* 2005, 77, 615.

[33] T. Schafer, F. Di Francesco, R. Fuoco, *Microchem. J.* 2007, 85, 52.

[34] R. D. Rogers, *Nature* 2007, 447, 917.

[35] X. M. Xu, C. Z. Li, K. M. Pei, K. Zhao, Z. B. K. Zhao, H. Y. Li, *Sens. Actuators, B* 2008, 134, 258.

[36] X. M. Xu, H. W. Cang, C. Z. Li, Z. B. K. Zhao, H. Y. Li, *Talanta* 2009, 78, 711.

[37] A. Tesfai, B. El-Zahab, A. T. Kelley, M. Li, J. C. Garno, G. A. Baker, I. M. Warner, *ACS Nano* 2009, 3, 3244.

[38] C. P. Fredlake, J. M. Crosthwaite, D. G. Hert, S. Aki, J. F. Brennecke, *J. Chem. Eng. Data* 2004, 49, 954.

[39] C. F. Kahle, *Ind. Eng. Chem. Res.* 2001, 40, 33.

[40] D. Z. Shen, X. Y. Li, Q. Kang, H. T. Zhang, Y. Qi, *Anal. Chim. Acta* 2006, 566, 19.

[41] H. Muramatsu, E. Tamiya, I. Karube, *Anal. Chem.* 1988, 60, 2142.

[42] L. M. Ilharco, R. B. de Barros, *Langmuir* 2000, 16, 9331.

[43] S. A. Katsyuba, E. E. Zvereva, A. Vidis, P. J. Dyson, *J. Phys. Chem. A* 2007, 111, 352.

[44] J. Y. Wang, H. B. Chu, Y. Li, *ACS Nano* 2008, 2, 2540.

[45] A. C. Puleo, D. R. Paul, S. S. Kelley, *J. Membr. Sci.* 1989, 47, 301.

[46] S. L. Ma, Y. T. Wu, M. L. Hurrey, S. L. Wallen, C. S. Grant, *J. Phys. Chem. B* 2010, 114, 3809.

[47] A. Erol, S. Okur, N. Yağmurcukardŝ, M. Ç. Arikan, *Sens. Actuators, B* 2011, 152, 115.

[48] N. Uzar, S. Okur, M. C. Arikan, *Sens. Actuators, A* 2011, 167, 188.

[49] Y. Fu, H. O. Finklea, *Anal. Chem.* 2003, 75, 5387.

[50] A. F. Holloway, A. Nabok, M. Thompson, A. K. Ray, D. Crowther, J. Siddiqi, *Sensors* 2003, 3, 187.

[51] J. S. Vrentas, J. L. Duda, *J. Polym. Sci. Part B: Polym. Phys.* 1977, 15, 403.

[52] G. Dlubek, Y. Yu, R. Krause-Rehberg, W. Beichel, S. Bulut, N. Pogodina, I. Krossing, C. Friedrich, *J. Chem. Phys.* 2010, 133, 124502.

[53] L. Ferguson, P. Scovazzo, *Ind. Eng. Chem. Res.* 2007, 46, 1369.

[54] L. A. Blanchard, Z. Y. Gu, J. F. Brennecke, *J. Phys. Chem. B* 2001, 105, 2437.

[55] W. Makino, R. Kishikawa, M. Mizoshiri, S. Takeda, M. Yao, *J. Chem. Phys.* 2008, 129, 104510.

[56] S. J. Martin, G. C. Frye, S. D. Senturia, *Anal. Chem.* 1994, 66, 2201.

[57] A. L. Smith, J. N. Ashcraft, P. T. Hammond, *Thermochim. Acta* 2006, 450, 118.

[58] E. Tellechea, D. Johannsmann, N. F. Steinmetz, R. P. Richter, I. Reviakine, *Langmuir* 2009, 25, 5177.

[59] A. Katz, M. D. Ward, *J. Appl. Phys.* 1996, 80, 4153.

[60] N. I. Sakellarios, S. G. Kazarian, in *Ionic Liquids IIIA: Fundamentals, Progress, Challenges, and Opportunities, Properties and Structure*, Vol. 901 (Eds: R. D. Rogers, K. R. Seddon), Amer Chemical Soc, Washington 2005, 89.

[61] H. Chen, M. L. Cheng, Y. C. Jean, L. J. Lee, J. Yang, *J. Polym. Sci., Part B: Polym. Phys.* 2008, 46, 388.

[62] C. D. Sorrell, L. A. Lyon, *J. Phys. Chem. B* 2007, 111, 4060.

[63] B. Hess, C. Kutzner, D. van der Spoel, E. Lindahl, *J. Chem. Theory Comput.* 2008, 4, 435.

[64] G. Bussi, D. Donadio, M. Parrinello, *J. Chem. Phys.* 2007, 126, 014101.

[65] G. Bussi, T. Zykova-Timan, M. Parrinello, *J. Chem. Phys.* 2009, 130, 074101.

[66] D. Y. Tom Darden, and Lee Pedersen, *J. Chem. Phys.* 1993, 98, 10089.

[67] B. Hess, H. Bekker, H. J. C. Berendsen, J. Fraaije, *J. Comput. Chem.* 1997, 18, 1463.

[68] W. L. Jorgensen, D. S. Maxwell, J. Tiradorives, *J. Am. Chem. Soc.* 1996, 118, 11225.

[69] J. N. C. Lopes, J. Deschamps, A. A. H. Padua, *J. Phys. Chem. B* 2004, 108, 2038.

[70] J. N. C. Lopes, A. A. H. Padua, K. Shimizu, *J. Phys. Chem. B* 2008, 112, 5039.

The complete disclosures of all references cited above and throughout the specification are hereby incorporated by reference in their entirety, as are the complete disclosures of the two priority applications, Ser. No. 61/434,660 and Ser. No. 61/434,879. In the event of an otherwise irresolvable conflict, however, the disclosure of the present specification shall control.

What is claimed:

1. A composite material comprising an intermixture of one or more GUMBOS with one or more polymers, wherein:
    (a) each of said GUMBOS is an organic salt having a melting point between 25° C. and 250° C.; wherein an organic salt is a salt comprising at least one organic anion, or at least one organic cation, or both an organic anion and an organic cation;
    (b) said composite material is viscoelastic; and the viscoelastic characteristics of said composite material are substantially different from what the viscoelastic characteristics of the GUMBOS alone would be, if the GUMBOS were not intermixed with the one or more polymers;
    (c) each of said one or more GUMBOS is amorphous within said composite material.

2. The composite material of claim 1, wherein the rigidity of said composite material is substantially different from the rigidity that the GUMBOS alone would possess, if the GUMBOS were not intermixed with the one or more polymers.

3. An article of manufacture, comprising a piezoelectric crystal coated with a film, wherein said film comprises the composite material of claim 1.

4. The article of manufacture of claim 3, wherein said piezoelectric crystal comprises quartz.

5. The article of manufacture of claim 3 wherein, following the absorption of gas molecules by said film, the change in the motional resistance of said piezoelectric crystal is a linear function of the number of absorbed gas molecules, and the change in the motional resistance of said piezoelectric crystal is independent of the chemical properties of the absorbed gas molecules.

6. A crystal microbalance comprising the article of manufacture of claim 5.

7. A method of detecting one or more volatile organic compounds with the crystal microbalance of claim 6, said method comprising measuring changes in the motional resistance of the piezoelectric crystal in the presence of the one or more volatile organic compounds, or measuring changes in the frequency of the piezoelectric crystal in the presence of the one or more volatile organic compounds, or both; wherein a change in the motional resistance or a change in the frequency indicates that one or more volatile compounds have been absorbed by the film.

8. An array comprising a plurality of the crystal microbalances of claim 6, wherein each of said crystal microbalances comprises a film of a different said composite material, wherein the different said crystal microbalances possess differing sensitivities to different compounds; whereby the selectivity of the array to discriminate between different compounds is enhanced as compared to the selectivity of any of the individual said crystal microbalances.

9. A method of determining the molecular weight, M.W., of a volatile organic compound with the crystal microbalance of claim 6, said method comprising measuring the change, $\Delta R$, in the motional resistance of the piezoelectric crystal in the presence of the volatile organic compound, and measuring the change, $\Delta f$, in the frequency of the piezoelectric crystal in the presence of the volatile organic compound; and calculating $M.W.=\Delta f/(k \cdot \Delta R)$; wherein k is a proportionality constant that is characteristic of the crystal microbalance, the composition of the composite, and the mass of the film per unit area on the surface of the piezoelectric crystal; and wherein the proportionality constant k is independent of the chemical properties of the volatile organic compound.

* * * * *